(12) United States Patent
Gan

(10) Patent No.: US 7,893,934 B2
(45) Date of Patent: Feb. 22, 2011

(54) THREE-DIMENSIONAL FINITE ELEMENT MODELING OF HUMAN EAR FOR SOUND TRANSMISSION

(75) Inventor: Rong Z. Gan, Oklahoma City, OK (US)

(73) Assignee: The Board of Regents of the University of Oklahoma, Norman, OK (US)

( * ) Notice: Subject to any disclaimer, the term of this patent is extended or adjusted under 35 U.S.C. 154(b) by 410 days.

(21) Appl. No.: 11/441,541

(22) Filed: May 26, 2006

(65) Prior Publication Data
US 2006/0278245 A1    Dec. 14, 2006

Related U.S. Application Data

(60) Provisional application No. 60/685,026, filed on May 26, 2005.

(51) Int. Cl.
*G06T 15/00* (2006.01)
(52) U.S. Cl. ...................................................... 345/419
(58) Field of Classification Search .................. 345/419
See application file for complete search history.

(56) References Cited

U.S. PATENT DOCUMENTS

| | | | | |
|---|---|---|---|---|
| 5,176,620 | A * | 1/1993 | Gilman | 600/25 |
| 2002/0066310 | A1 * | 6/2002 | Jachim | 73/159 |
| 2006/0225509 | A1 * | 10/2006 | Haupt et al. | 73/649 |

OTHER PUBLICATIONS

Sun et al.; Computer-integrated finite element modeling of human middle ear; Biomechanics and Modeling in Mechanobiology; Oct. 1, 2002; Springer Berlin / Heidelberg; vol. 1, No. 2; pp. 109-122.*

Sun et al.; "Three-Simensional Finite Element Modeling of Human Ear for Sound Transmission"; Jun. 2004; Springer Netherlands; vol. 32, No. 6; pp. 847-859.*

Gan, R. Z., and Q. Sun, "Finite Element Modeling of Human Ear with External Ear Canal and Middle Ear Cavity", Proceedings of the Second Joint EMBSIBMES Conference. (2002) pp. 264-265.

E. W. Abel, and R. M. Lord, "A Finite-Element Model for Evaluation of Middle Ear Mechanics", Papers from 23rd Annual International Conference of the IEEE Engineering in Medicine and Biology Society. (2001) pp. 1-3.

L. F. Martha, and E. Parente Junior, "An Object-Oriented Framework for Finite Element Programming", WCCM V Fifth World Congress on Computational Mechanics. (2002) pp. 1-10.

(Continued)

*Primary Examiner*—Xiao M Wu
*Assistant Examiner*—David T Welch
(74) *Attorney, Agent, or Firm*—Dunlap Codding, P.C.

(57) ABSTRACT

A finite element model of an ear stored on a computer readable medium having logic representing a three-dimensional geometric model of the ear; logic for meshing individual anatomical structures of the ear accounting for whether the anatomical structures include at least one of air, liquid material and solid material; logic for assigning material properties for each anatomical structure based on at least one physical property of each anatomical structure; logic for assigning boundary conditions for some of the anatomical structures indicative of interaction between such anatomical structures; and logic for employing acoustic-structural coupled analysis to the anatomical structures of the ear to generate data indicative of the acoustic effect on mechanical vibration transmission in the ear.

Various embodiments of "one-chamber" and "two-chamber" analyses and models are described.

18 Claims, 23 Drawing Sheets

OTHER PUBLICATIONS

Sun, Q. et al., Computer-integrated finite element modeling of human middle ear, Biomechanics and Modeling in Mechanobiology, Oct. 2002, pp. 109-122, vol. 1, No. 2, Springer-Verlag.

Gan, Rong Z., Three-dimensional Modeling of Middle Ear Biomechanics and Its Applications, Otology & Neurotology, pp. 271-280, vol. 23, No. 3, 2002.

Gan, Rong Z., Three-dimensional Finite Element Modeling of Human Ear for Sound Transmission, Biomedical Engineering Society, pp. 847-859, vol. 32, No. 6, Jun. 2004.

Gan, Rong Z., Acoustic-structural coupled finite element analysis for sound transmission in human ear—Pressure distributions, Medical Engineering & Physics 28, pp. 395-404, Elsevier Ltd, 2006.

* cited by examiner

| Structure | The FE Model | Our previous FE Model | Published data |
|---|---|---|---|
| Eardrum | | | |
| Diameter along manubrium (mm) | 10.86 | 8.76 | 8.0–10.0 (Gray, 1918[a]) |
| Diameter perpendicular to manubrium (mm) | 9.24 | 8.93 | 7.5–9.0 (Helmholtz, 1863[a]) |
| Height of the cone (mm) | 1.46 | 1.46 | 2.0 (Siebenmann, 1897[a]) |
| Surface area (mm$^2$) | 72.01 | 66.30 | 55.8–85.0 (Wever & Lawrence[30]; Keith, 1918[a]; Békésy, 1941[a]) |
| Thickness (mm) | 0.05–0.10 | 0.05–0.074 | 0.1 (Helmholtz, 1863[a]), 0.04–0.075 (Kirikae[14]) |
| Malleus | | | |
| Length from the end of manubrium to the end of lateral process (mm) | 4.71 | 4.20 | 5.8 (Stuhlman, 1937[a]) |
| Total length (mm) | 8.11 | 7.65 | 7.6–9.1 (Bast & Anson, 1949[a]) |
| Density (average) (kg/m$^3$) | $3.59 \times 10^3$ | $3.59 \times 10^3$ | 3.59 (Kirikae[14]) |
| Weight (mg) | 30.42 | 23.94 | 23–27 (Stuhlman, 1937[a]; Wever & Lawrence[30]) |
| Incus | | | |
| Length along long process (mm) | 6.02 | 6.08 | 7.0 (Stuhlman, 1937[a]) |
| Length along short process (mm) | 4.58 | 4.49 | 5.0 (Stuhlman, 1937[a]) |
| Density (average) (kg/m$^3$) | $3.23 \times 10^3$ | $3.23 \times 10^3$ | $3.23 \times 10^3$ (Kirikae[14]) |
| Weight (mg) | 26.47 | 24.77 | 25–32 (Stuhlman, 1937[a]; Wever & Lawrence[30]) |
| Stapes | | | |
| Height (mm) | 2.66 | 2.87 | 2.5–4.0 (Stuhlman, 1937[a]; Wever & Lawrence[30]) |
| Length of footplate (mm) | 2.64 | 2.5 | 2.64–3.36 (Wever & Lawrence[30]); 2.5 (our measurement) |
| Width of footplate (mm) | 1.32 | 1.38 | 0.7–1.66 (Helmholtz, 1863[a]; Wever & Lawrence[30]) |
| Density (kg/m$^3$) | $2.20 \times 10^3$ | $2.20 \times 10^3$ | $2.20 \times 10^3$ (Kirikae[14]) |
| Weight (mg) | 1.93 | 2.24 | 2.05–4.35 (Wever & Lawrence[30]) |

[a]The data come from Wever and Lawrence.[30]

*Table 1*

| Structure | The FE Model |
|---|---|
| TM <br> Density <br> Young's Modulus <br> (pars tensa) <br><br> (pars flaccida) | 1.2×10$^3$ kg/m$^3$ <br><br> 3.5×10$^7$ N/m$^2$ (radial) <br> 2.0×10$^7$ N/m$^2$ (circumferential) <br> 1.0×10$^7$ N/m$^2$ (radial) <br> 1.0×10$^7$ N/m$^2$ (circumferential) |
| Malleus <br> Density    (head) <br>          (neck) <br>          (handle) <br>          (average) <br> Weight | 2.55×10$^3$ kg/m$^3$ <br> 4.53×10$^3$ kg/m$^3$ <br> 3.70×10$^3$ kg/m$^3$ <br> 3.59×10$^3$ kg/m$^3$ <br> 30.42 mg |
| Young's Modulus | 1.41×10$^{10}$ N/m$^2$ |
| Incus <br> Density    (body) <br>          (short process) <br>          (long process) <br>          (average) <br> Weight | 2.36×10$^3$ kg/m$^3$ <br> 2.26×10$^3$ kg/m$^3$ <br> 5.08×10$^3$ kg/m$^3$ <br> 3.23×10$^3$ kg/m$^3$ <br> 26.47 mg |
| Young's Modulus | 1.41×10$^{10}$ N/m$^2$ |
| Stapes <br> Density <br> Weight <br> Young's Modulus | 2.20×10$^3$ kg/m$^3$ <br> 1.93 mg <br> 1.41×10$^{10}$ N/m$^2$ |
| Incudomalleolar Joint <br> Density <br> Young's Modulus | 3.2×10$^3$ kg/m$^3$ <br> 1.41×10$^{10}$ N/m$^2$ |
| Incudostapedial Joint <br> Density <br> Young's Modulus | 1.2×10$^3$ kg/m$^3$ <br> 6.0×10$^5$ N/m$^2$ |
| Manubrium <br> Density <br> Young's Modulus | 1.0×10$^3$ kg/m$^3$ <br> 4.7×10$^9$ N/m$^2$ |

*Table 1A*

| Structure | The FE Model | Sources |
|---|---|---|
| Eardrum | | |
| Density (kg/m$^3$) | $1.2 \times 10^3$ | $1.2 \times 10^3$ (Wada & Metoki[28]) |
| Young's Modulus (N/m$^2$) | | $2.0 \times 10^7$ (Békésy[27]) |
| Pars tensa | $3.5 \times 10^7$ (radial) | $4.0 \times 10^7$ (Kirikae[14]) |
| | $2.0 \times 10^7$ (circumferential) | |
| Pars flaccida | $1.0 \times 10^7$ (radial) | |
| | $1.0 \times 10^7$ (circumferential) | |
| Malleus | | |
| Density (kg/m$^3$) | | |
| Head | $2.55 \times 10^3$ | $2.55 \times 10^3$ (Kirikae[14]) |
| Neck | $4.53 \times 10^3$ | $4.53 \times 10^3$ (Kirikae[14]) |
| Handle | $3.70 \times 10^3$ | $3.70 \times 10^3$ (Kirikae[14]) |
| Young's Modulus (N/m$^2$) | $1.41 \times 10^{10}$ | $1.41 \times 10^{10}$ (Herrmann & Liebowitz[11]) |
| Incus | | |
| Density (kg/m$^3$) | | |
| Body | $2.36 \times 10^3$ | $2.36 \times 10^3$ (Kirikae[14]) |
| Short process | $2.26 \times 10^3$ | $2.26 \times 10^3$ (Kirikae[14]) |
| Long process | $5.08 \times 10^3$ | $5.08 \times 10^3$ (Kirikae[14]) |
| Young's Modulus (N/m$^2$) | $1.41 \times 10^{10}$ | $1.41 \times 10^{10}$ (Herrmann & Liebowitz[11]) |
| Stapes | | |
| Density (kg/m$^3$) | $2.20 \times 10^3$ | $2.20 \times 10^3$ (Kirikae[14]) |
| Young's Modulus (N/m$^2$) | $1.41 \times 10^{10}$ | $1.41 \times 10^{10}$ (Herrmann & Liebowitz[11]) |
| Incudomalleolar Joint | | |
| Density (kg/m$^3$) | $3.2 \times 10^3$ | $3.2 \times 10^3$ (Sun et al.[26]) |
| Young's Modulus (N/m$^2$) | $1.41 \times 10^{10}$ | $1.41 \times 10^{10}$ (Sun et al.[26]) |
| Incudostapedial Joint | | |
| Density (kg/m$^3$) | $1.2 \times 10^3$ | $1.2 \times 10^3$ (Sun et al.[26]) |
| Young's Modulus (N/m$^2$) | $6.0 \times 10^5$ | $6.0 \times 10^5$ (Wada et al.[29], Prendergast et al.[22]) |
| Manubrium | | |
| Density (kg/m$^3$) | $1.0 \times 10^3$ | $1.0 \times 10^3$ (Sun et al.[26]) |
| Young's Modulus (N/m$^2$) | $4.7 \times 10^9$ | $4.7 \times 10^9$ (Sun et al.[26]) |

*Table 2*

| Ligaments | Young's Modulus (N/m$^2$) |
|---|---|
| Superior mallear ligament (C1) | $4.9 \times 10^6$ |
| Lateral mallear ligament (C2) | $6.7 \times 10^6$ |
| Posterior incudal ligament (C3) | $6.5 \times 10^6$ |
| Anterior mallear ligament (C4) | $2.1 \times 10^7$ |
| Posterior stapedial tendon (C5) | $5.2 \times 10^7$ |
| Tensor tympani tendon (C7) | $7.0 \times 10^7$ |
| Tympanic annular ligament | $6.0 \times 10^5$ |
| Stapedial annular ligament | $2.0 \times 10^5$ |

*Table 2A*

| Ligaments | Young's Modulus (N/m$^2$) or Spring Constant (N/m) | |
|---|---|---|
| | The FE Model | Our previous FE Model |
| Superior mallear ligament (C1) (N/m$^2$) | $4.9 \times 10^6$ | $1.0 \times 10^5$ (Gan et al.[7]) |
| Lateral mallear ligament (C2) (N/m$^2$) | $6.7 \times 10^6$ | $1.0 \times 10^5$ (Gan et al.[7]) |
| Posterior incudal ligament (C3) (N/m$^2$) | $6.5 \times 10^6$ | $6.5 \times 10^5$ (Wada et al.[29]; Prendergast et al.[22]) |
| Anterior mallear ligament (C4) (N/m$^2$) | $2.1 \times 10^7$ | $2.1 \times 10^6$ (Gan et al.[7]; Sun et al.[26]) |
| Posterior stapedial tendon (C5) (N/m$^2$) | $5.2 \times 10^7$ | $5.2 \times 10^5$ (Wada et al.[29]; Prendergast et al.[22]) |
| Tensor tympani tendon (C7) (N/m$^2$) | $7.0 \times 10^7$ | $2.6 \times 10^6$ (Wada et al.[29]; Prendergast et al.[22]) |
| Tympanic annulus (N/m$^2$) | $6.0 \times 10^5$ | $6.0 \times 10^5$ (Gan et al.[7]; Sun et al.[26]) |
| Stapedial annular ligament (N/m) | 40 | 9 (converted from Lynch et al.[19]) |

*Table 3*

THREE-DIMENSIONAL FINITE ELEMENT MODELING OF HUMAN EAR FOR SOUND TRANSMISSION

CROSS-REFERENCE TO RELATED APPLICATIONS

The present patent application claims priority to the provisional patent application identified by U.S. Ser. No. 60/685,026 filed on May 26, 2005, the entire content of which is hereby incorporated herein by reference.

STATEMENT REGARDING FEDERALLY SPONSORED RESEARCH OR DEVELOPMENT

Not Applicable.

THE NAMES OF THE PARTIES TO A JOINT RESEARCH AGREEMENT

Not Applicable.

REFERENCE TO A "SEQUENCE LISTING," A TABLE, OR A COMPUTER PROGRAM LISTING APPENDIX SUBMITTED ON A COMPACT DISC AND AN INCORPORATION-BY-REFERENCE OF THE MATERIAL ON THE COMPACT DISC

Not Applicable.

BACKGROUND OF THE INVENTION

The ear transfers sound through the external ear canal and middle ear into the inner ear (cochlea). The external ear canal collects sound pressure waves and transfers them to the tympanic membrane. The middle ear, which includes tympanic membrane (or eardrum) and three ossicular bones (i.e., malleus, incus and stapes) suspended in an air-filled cavity (i.e., middle ear cavity) by suspensory ligaments/muscles, is an extremely small structure with complex shape. Sound collected in the ear canal entry and passed to the middle ear through the tympanic membrane (TM) initiates the acoustic-mechanical transmission in the ear. The middle ear builds a mechanism (ossicular chain) for transmitting vibrations of the TM to the fluid in cochlea. A number of parameters such as the shape and stiffness of the TM, shape and volume of the external ear canal, and volume and pressure of the middle ear cavity directly affect acoustic-mechanical transmission through the ear. Changes of these parameters are often related to patho-physiological conditions in the ear.

Since the transfer function of the middle ear cannot be measured readily in living humans, various different theoretical modeling methods have been developed to simulate the functions of the ear. Among them, analogy-modeling method (represented by circuit or lumped parameter models) proved to be an important tool and was widely employed in the ear mechanics[32, 31, 33, 17, 10, 34]. Other quantitative middle ear models, including analytical model[23] and multibody model[12] also presented valuable findings in predicting normal and pathological mechanics of the middle ear. Early modeling of middle ear function used a transformer analogy with circuit models or lumped parameter models reported by Zwislocki[31], Kringlebotn[17], and Hudde & Weistenhöfer[12].

While the analytical approach worked reasonably well for some limited situations, it was not always possible to model the realistic acoustic-mechanical response in the ear involving complex geometry and an array of material compositions. The finite element (FE) method, a general numerical procedure, has distinct advantages over analytical approaches in modeling complex biological systems. The FE method is always capable of modeling the complex geometry, ultrastructural characteristics, and non-homogenous and anisotropic material properties of biological systems. FE models can also determine the detailed vibration shapes, stress distributions, and dynamic behaviors at any locations in a system, which is not possible with analytical solutions. The first FE model of the ear (for cat eardrum) was reported by Funnell and Laszlo in 1978.[5] In 1992, a three-dimensional (3-D) FE model of middle ear was published by Wada and Metoki[28] to investigate vibration patterns of the middle ear system. Since then, FE modeling of the static and dynamic behaviors of the middle ear subsets or entire middle ear has become a rapidly growing research area in ear mechanics.[15,13,17] A thorough literature survey about the FE modeling of ear mechanics was summarized in a previous publication.[26]

Using the combined technologies of FE analysis and 3-D reconstruction of human middle ear, a geometric (computer-aided design (CAD)) model and FE model of the middle ear was constructed based on a set of digitized section images of one human temporal bone (right ear, age 52, female).[7,25,26] To date, this FE model may represent the best geometric configurations of the middle ear ossicles and eardrum and has the capability for analysis on transmission of sound pressure-induced vibrations through the middle ear. However, this FE model needs further improvements to include the external ear canal, middle ear cavity, and cochlea in order to simulate the complete acoustic-mechanical transmission in the ear. The individual variation of temporal bones in geometry and material properties also needs to be identified through models constructed from different temporal bones.

Using the combined technologies of FE analysis and 3D reconstruction of the middle ear, the first FE model of human middle ear with the TM, ossicular bones, middle ear ligaments/muscle tendons, and middle ear boundaries[7, 25, 26] was developed. However, the ear is a complex system formed of air, liquid and mechanical structures making the function of the ear a very difficult system to understand and simulate. Thus, there remained a need to accurately model the interactions between the various anatomical structures of the ear including the acoustic-mechanical transmission through the ear. It is to such an improved model of the ear that the present invention is directed.

SUMMARY OF THE INVENTION

In general, the present invention relates to a computational model of an ear, such as a human ear. More specifically, the present invention relates to a computational model of a human ear which is constructed using a three-dimensional finite element technique and simulates the interactions between the various anatomical structures of the ear including the acoustic-mechanical transmission through the ear.

A human ear consists of three main parts: an outer ear, a middle ear, and an inner ear. The outer ear comprises an ear canal. Since the transfer function of the middle ear and other structures of the ear cannot be measured readily in living humans, theoretical modeling is generally used to simulate the functions of the ear.

Due to its complexity, analysis for sound transmission in the human ear involves various different factors, such as solid structures (e.g., soft tissues, bones), acoustics (e.g., air or other mediums such as water or oil in the ear canal and middle ear cavity), and fluid (e.g., cochlear fluid). Each of these factors involves different engineering disciplines, boundary conditions, element attributes and model parameters. By computationally accounting for these considerations in a finite element (FE) model, the present invention offers a method and system which more accurately models the various anatomical structures of the ear, such as a human ear, various artificial or natural conditions or acoustical structures applied to or naturally occurring within the ear, such as hearing aids or various mediums such as water, oil or gas, and the acoustic—mechanical transmission through the ear. FE modeling, which involves a numerical procedure, is capable of modeling the complex geometry, ultrastructural characteristics, and nonhomogeneous and anisotropic material properties of the human ear system. FE modeling can also be used to determine the detailed vibration shapes, stress distributions, and dynamic behaviors at any location in the ear system.

The accurate and comprehensive FE model of the present invention has sufficient functional feasibility for analyzing and predicting the dynamics of the human ear under normal and pathological conditions, as well as reconstructed and implanted conditions. As such, the FE model of the present invention can be applied to a broad number of applications, such as (1) diagnosis of conditions of the ear, (2) design of implantable hearing devices, (3) evaluation of implantable devices or surgical treatment and combinations thereof. Thus, it can improve the basic understanding of the hearing mechanism and sound transmission of the ear. It can also be used to assess the influence of ear diseases on hearing by simulating structural or environmental alterations of the ear caused by diseases. Further, it can facilitate the diagnosis and the treatment of hearing loss. For example, the computational FE model of the present invention can be incorporated into clinical tools to improve diagnostic effectiveness for ear diseases, such as otitis media, TM perforation, otoscelerosis, or ossicular disarticulations and fixation. Also, surgical approaches or treatments performed to restore hearing can be computationally evaluated. Furthermore, the FE model of the present invention can be used to research and evaluate the design and performance of middle ear implants and implantable hearing devices. For example, it can be used to determine the effects of implanted actuators or transducers on the middle ear ossicular and cochlear functions. It can also be used to evaluate electromagnetic-mechanical coupling of devices which correlate electromagnetic fields into mechanical ear vibration.

In general, the present invention combines the technologies of three-dimensional reconstruction of human temporal bones and tissues, and finite element analysis of ear mechanics. This three-dimensional finite element technique is used to generate computational models of the anatomical structures of the ear, such as a human ear or other ear such as a mammalian ear, reptilian ear or the like, including the external ear canal, the middle ear, and the inner ear and then to model the interactions between the various anatomical structures (also referred to herein as "components") of the ear for sound transmission.

In one embodiment, the present invention is directed to a method for developing a computational model of an ear. In this method, a three-dimensional geometric model of the ear is constructed including various anatomical structures. Then, individual anatomical structures of the ear are meshed accounting for whether the anatomical structures include at least one of air, liquid material and solid material. Material properties are assigned for each anatomical structure based on at least one physical property of each anatomical structure. Boundary conditions are assigned for some of the anatomical structures indicative of interaction between such anatomical structures. Then, acoustic-structural coupled FE analysis is employed to the anatomical structures of the ear to generate data indicative of the acoustic effect on mechanical vibration transmission in the ear.

Preferably, the geometric model is constructed based on histological section images of a temporal bone of a human cadaver, which includes the ear canal, eardrum, middle ear cavity, ossicular chain, cochlea, Eustachian tube and semicircular canals. In one embodiment, the temporal bone is dissected into between about 500 and 1000 histological sections, and preferably about 700 to 800 histological sections, and more preferably about 780 histological sections, having a thickness of about 20 μm. The histological sections are scanned into a computer system (e.g., a Dell Dimensions 4100 personal computer system) so as to generate a plurality of digitized section images.

The digitized images of the temporal bone morphometry are utilized to reconstruct a three dimensional solid model in a computer program, such as the computer-aided design (CAD) software SolidWorks, which is accessible by the computer system. For example, the software can be stored on a memory device or other computer readable medium which is internal or external to the computer (e.g., a disk drive, a floppy disk, a CD, etc.), or accessible via an internet, intranet, or other network connection (e.g., a LAN, WAN, etc.)

The images are aligned, for example using fiducial marks provided in each image. The aligned images are then trimmed and brought onto a sketch plane in the CAD software. The aligned and treated images are then digitized by marking points along the outlines of the ear structures. Next, the images are segmented to generate a three-dimensional CAD model of the human ear. The CAD model is also suitable for solid freeform fabrication or rapid prototyping, thereby providing information needed to fabricate a visual, physical model of the human ear.

A next step of the method is to generate a finite element (FE) model of the ear based on the three-dimensional geometric model and the material properties and boundary conditions associated with the various anatomical structures of the ear. In one embodiment, the step of meshing the anatomical structures of the three-dimensional geometric model of the ear is implemented by importing the three-dimensional geometric model into a commercial FE pre- and post-processing software, such as HyperMesh software developed by Altair Computing, Inc., of Troy, Mich., which is accessible by the computer. Also, the boundary conditions or constraints of the ear structures and the material properties of each structure are assigned and then provided to the processing software. For example, the boundary conditions and material properties can be assigned from published data or determined by using a cross-calibration technique. The software then generates the FE model of the ear with a finite element mesh for each anatomical structure. Also, to include non-normal conditions, such as diseases or implanted devices, in the model, a theoretically calculated mass block or other representative object can be computationally added, or the properties of the existing model anatomical structures can be altered, so as to appropriately reflect the effects such conditions would have on the various anatomical structures of the normal ear.

In one embodiment, to investigate the functions of the ear utilizing the computational model of the present invention, a two-step scheme is utilized. First, structural analysis is employed to adjust and validate the FE model, and to study the mechanical functions of the middle ear. When harmonic sound pressure is applied on the TM from the ear canal side, the movement responses at different locations of the middle ear system are calculated through the FE structural analysis. Second, the acoustic-structural coupled analysis or acousticstructural-acoustic coupled analysis is employed to investigate the acoustic effect on mechanical vibration transmission in the ear using the validated FE model. To conduct the multi-field coupled FE analysis for sound transmission through the ear, a computer program accessible by the computer, such as ANSYS software developed by ANSYS Inc., of Canonsburg, Pa., can be utilized.

The computational model of the human ear of the present invention can include all or portions of the anatomical structures of the ear. In one embodiment, the computational model includes the eardrum, the middle ear ossicular bones (including the malleus, incus and stapes), and the middle ear suspensory ligaments or muscles. This embodiment can be used for example for middle ear structural analysis such as the vibration transmission through the middle ear under harmonic sound pressure applied on the eardrum. In another embodiment, the computational model includes the external ear canal, the eardrum, the ossicular bones, the suspensory ligaments and the middle ear cavity. This embodiment can be used for example for multi-field FE analysis such as the acoustic-structural coupled analysis on sound transmission from the ear canal to middle ear ossicles and cavity. In yet another embodiment, the computational model can include the external ear canal, the eardrum, the ossicular bones, the suspensory ligaments, the middle ear cavity, and the cochlea, so as to essentially model the entire ear and simulate the complete acoustic-mechanical transmission in the ear. This embodiment extends the middle ear mechanics into cochlea mechanics for comprehensive analysis of dynamic ear functions for sound transmission.

Once the FE model is constructed, it can be made available and modifiable for testing and other applications as a computer program containing the algorithms and data for the FE model. In this instance, the computer program is stored on a computer readable medium and typically includes (1) logic for representing a three-dimensional geometric model of the ear, (2) logic for meshing individual anatomical structures of the ear accounting for whether the anatomical structures include at least one of air, liquid material and solid material, (3) logic for assigning material properties for each anatomical structure based on at least one physical property of each anatomical structure, (4) logic for assigning boundary conditions for some of the anatomical structures indicative of interaction between such anatomical structures, and (5) logic for employing acoustic-structural coupled analysis to the anatomical structures of the ear to generate data indicative of the acoustic effect on mechanical vibration transmission in the ear. For example, the program can be software that is locally stored on a memory device or other computer readable medium which is internal or external to a computer (e.g., a disk drive, a floppy disk, a CD, etc.), or remotely accessible via an internet, intranet, or other network connection (e.g., a LAN, WAN, etc.). Further, it should be understood that the various logic forming the computer program can be distributed and stored and/or operated on by more than one computer readable medium or computer.

While other ear models exist, the computational FE model of the present invention has the following unique features: 1) it models accurate anatomical structures of the entire ear including normal, diseased and implanted ears, 2) it can readily provide information to facilitate the fabrication or rapid prototyping of a visual, physical model of the ear, 3) it allows for acoustic-mechanical (i.e., air-structure-fluid) coupled analysis on sound transmission through the ear, and 4) it allows for electromagnetic-mechanical or piezoelectric-mechanical coupled analysis of implantable hearing devices in the ear.

BRIEF DESCRIPTION OF THE SEVERAL
VIEWS OF THE DRAWING

So that the above recited features and advantages of the present invention can be understood in detail, a more particular description of the invention, briefly summarized above, may be had by reference to the embodiments thereof that are illustrated in the appended drawings. It is to be noted, however, that the appended drawings illustrate only typical embodiments of this invention and are therefore not to be considered limiting of its scope, for the invention may admit to other equally effective embodiments.

Figure 5A:
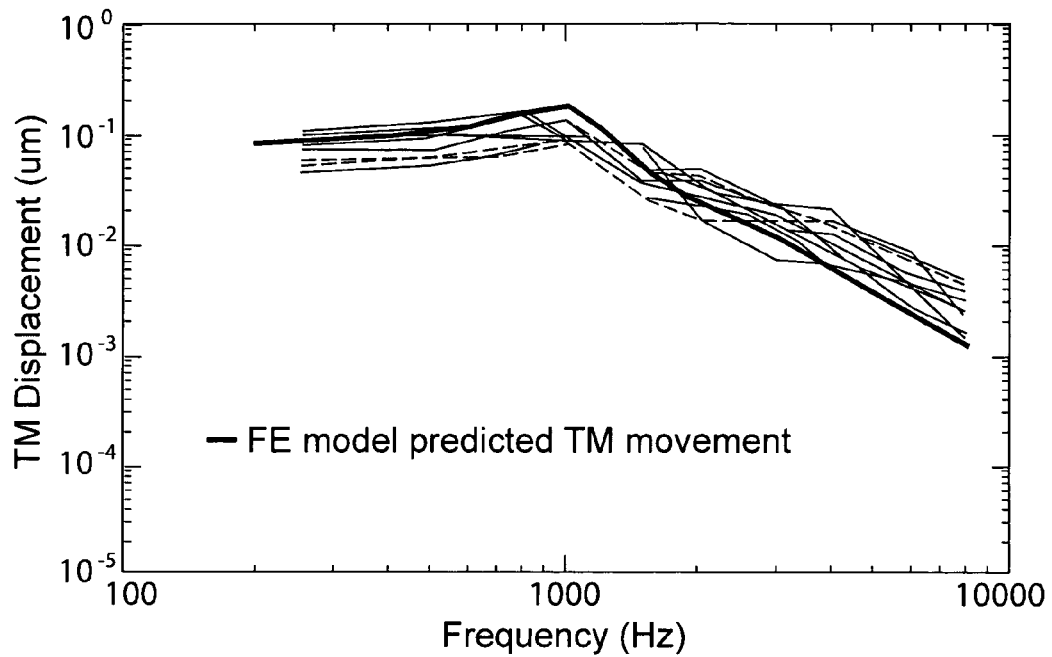
Figure 5B:
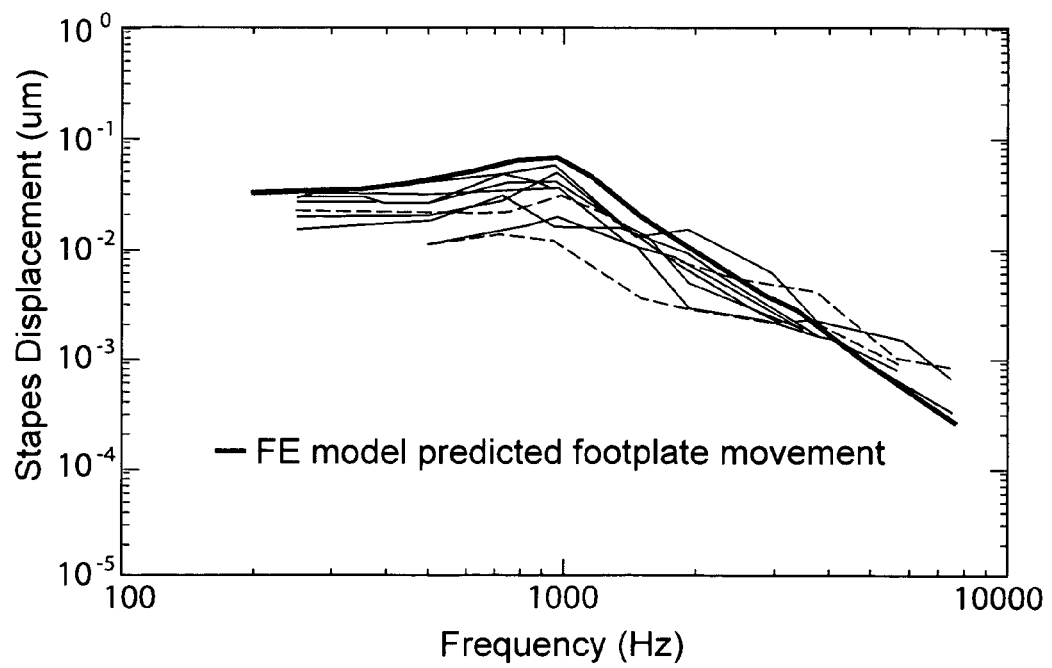

FIGS. 5A and 5B illustrate a comparison of the FE model-derived frequency response curves of the displacements at the tympanic membrane (FIG. 5A) and the stapes footplate (FIG. 5B) with the experimental data obtained from ten temporal bones[8] with the input sound pressure of 90 dB SPL at the TM. The thick solid lines represent the FE model prediction. Each thin line represents experimental data measured from an individual bone.

Figure 6A:
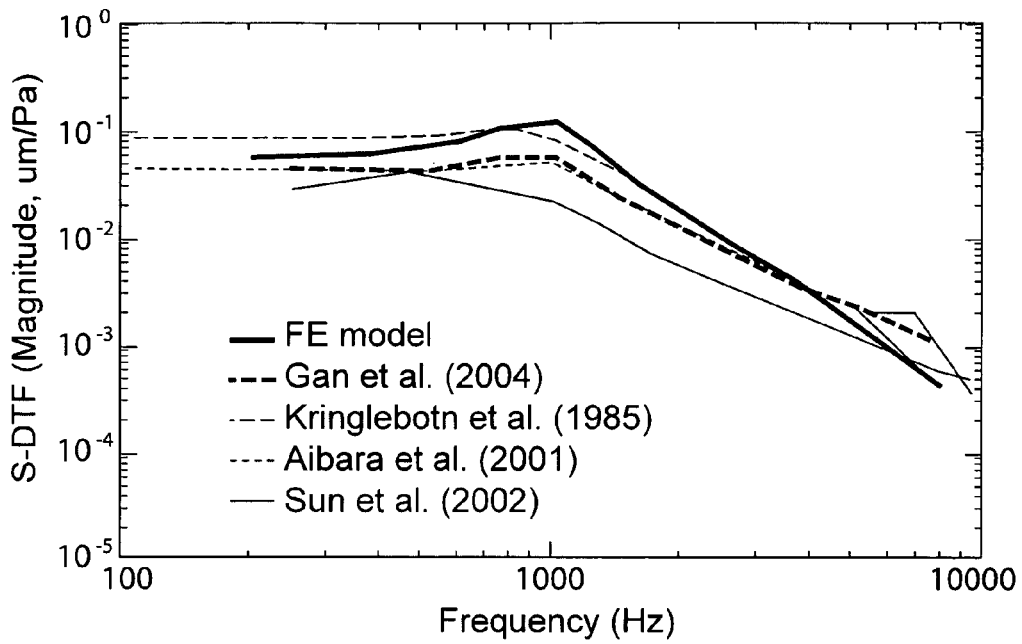
Figure 6B:
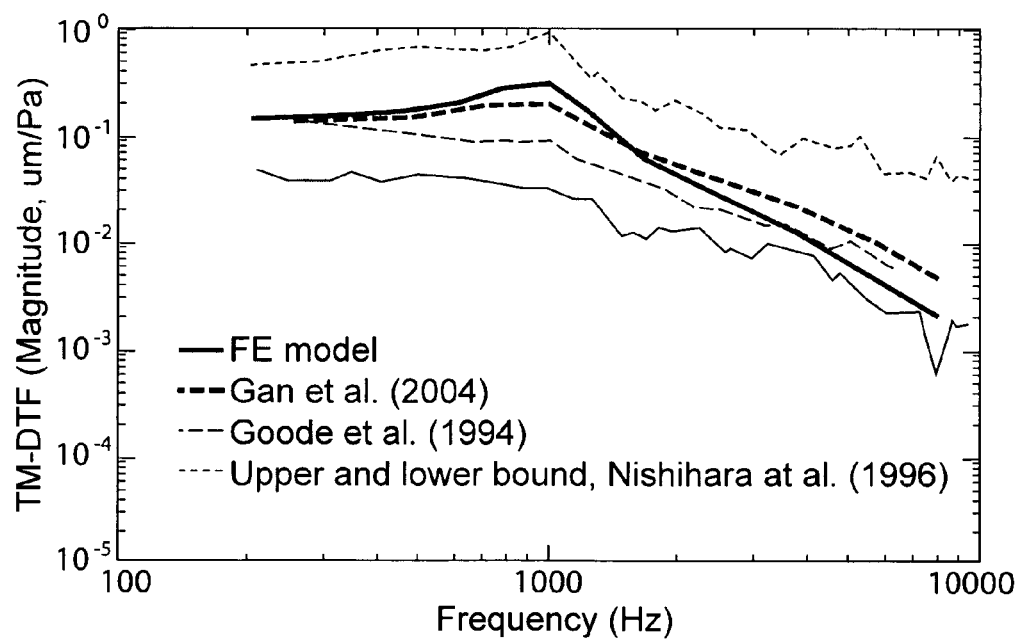

FIGS. 6A and 6B illustrate a comparison of the FE model-predicted stapes and TM displacement transfer functions with published data. Namely, FIG. 6A illustrates S-DTF obtained from the FE model compared with Kringlebotn and Gundersen[16], Aibara et al.[1], Gan et al.[8], and a previous FE model reported by Sun et al.[26] FIG. 6B illustrates TM-DTF obtained from the FE model compared with Goode et al.[10], Gan et al.[8] and Nishihara and Goode[21] experimental results.

Figure 7A:
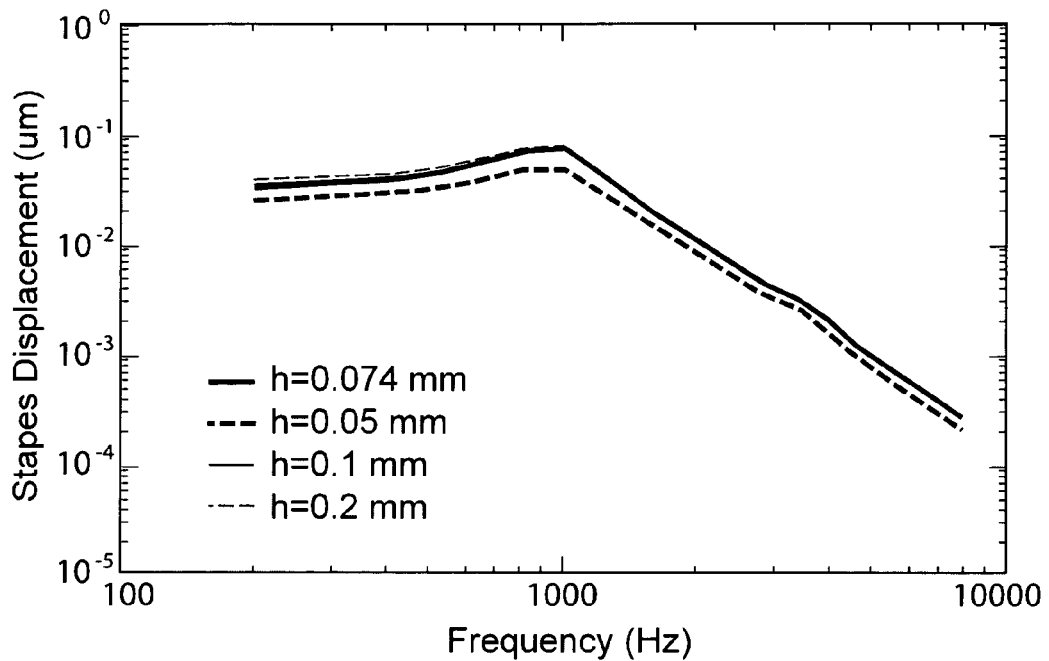
Figure 7B:
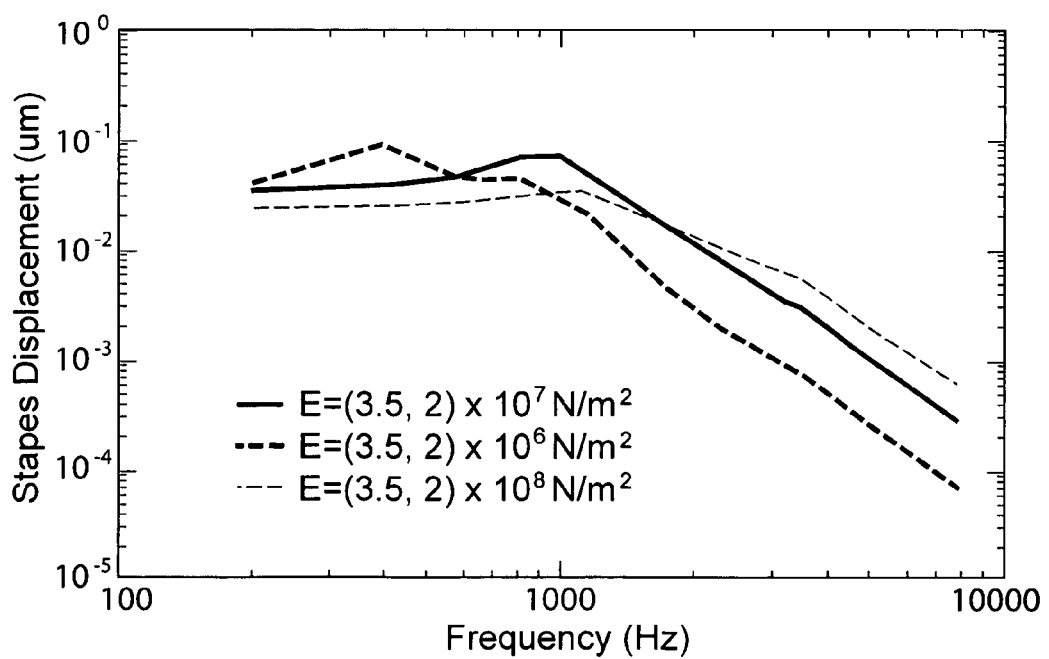

FIGS. 7A and 7B show (FIG. 7A) effect of the thickness of the TM on stapes footplate displacement as the thickness (h) changed from 0.05 to 0.2 mm; and (FIG. 7B) effect of the stiffness of the TM on stapes footplate displacement. The Young's modulus of the normal TM was assumed as $(3.5, 2.0) \times 10^7$ N/m$^2$ at pars tensa and $(1.0, 1.0) \times 10^7$ N/m$^2$ at pars flaccida (solid line). The first number in parentheses represents radial Young's modulus and the second number represents the circumferential modulus. The Young's modulus was reduced (thick broken line) or increased (thin broken line) by 10 fold from the normal value.

Figure 8A:
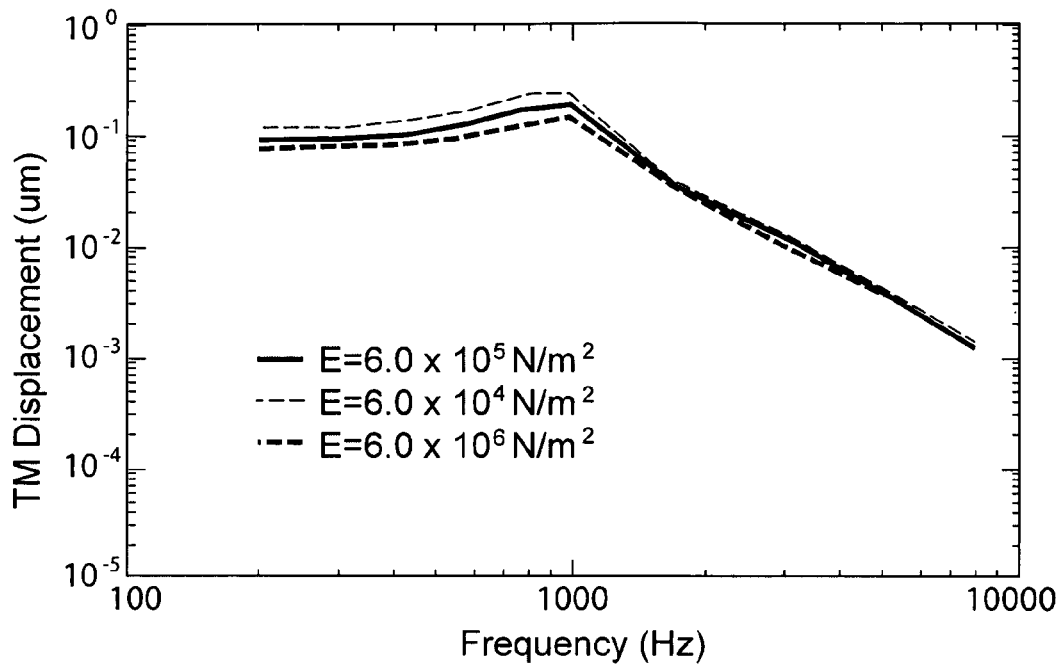
Figure 8B:
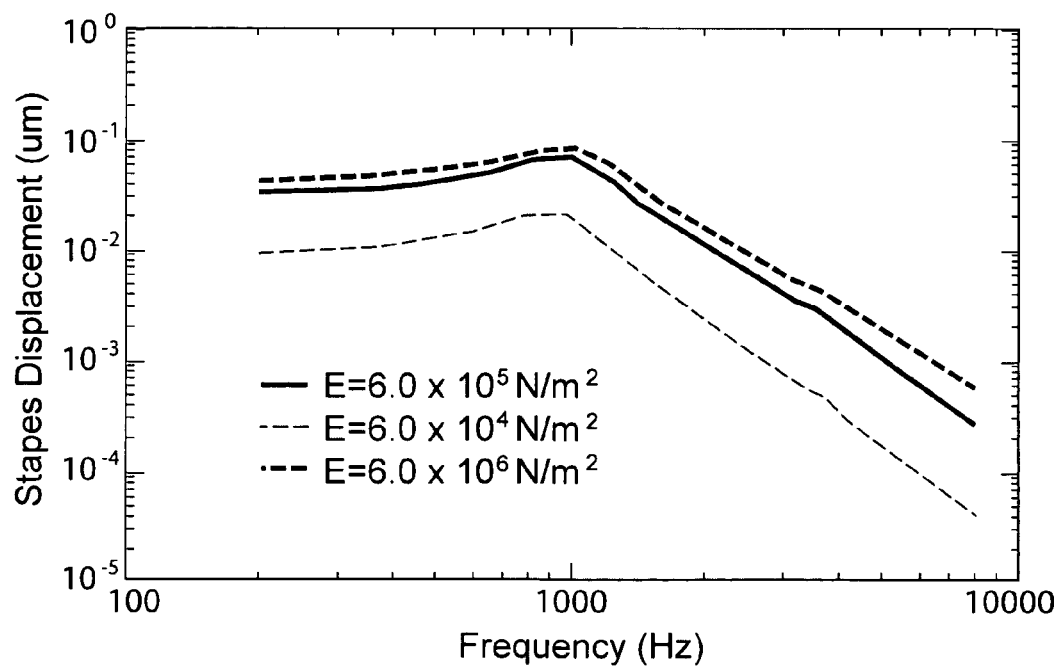

FIGS. 8A and 8B show the effects of material properties of the incudostapedial (I-S) joint on TM displacements (FIG. 8A) and stapes footplate displacements (FIG. 8B). The Young's modulus of the I-S joint was reduced (thin broken line) or increased (thick broken line) by a factor 10 from the normal value $6.0 \times 10^5$ N/m$^2$ (solid line) used for the model.

Figure 9A:
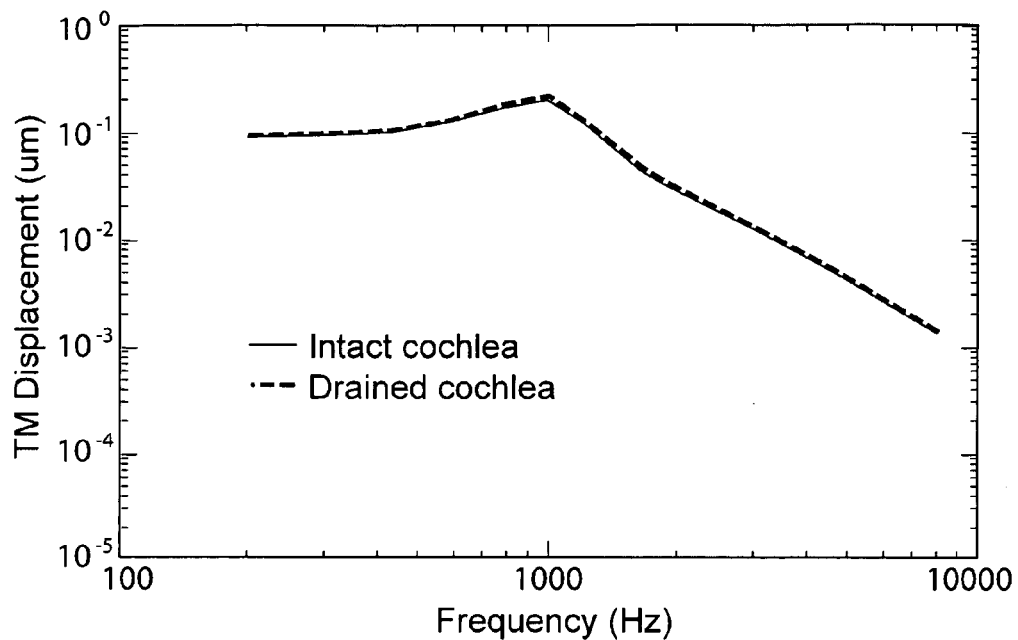
Figure 9B:
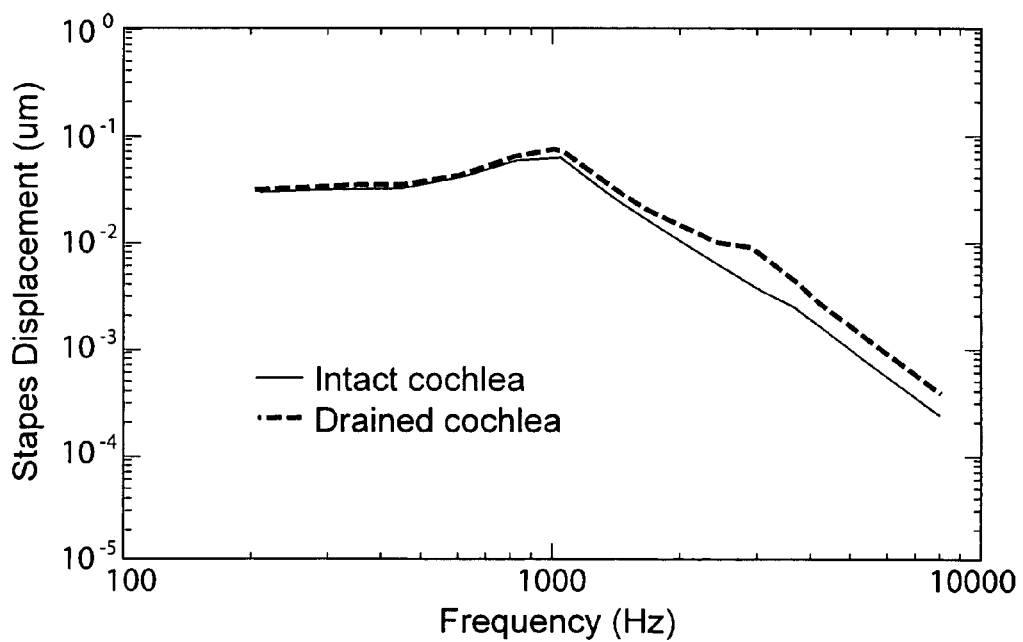

FIGS. 9A and 9B shows TM and stapes displacements obtained from the FE model for intact cochlea (solid lines) and drained cochlea (broken line). (A) TM displacement; (B) Stapes footplate displacement.

Figure 4:
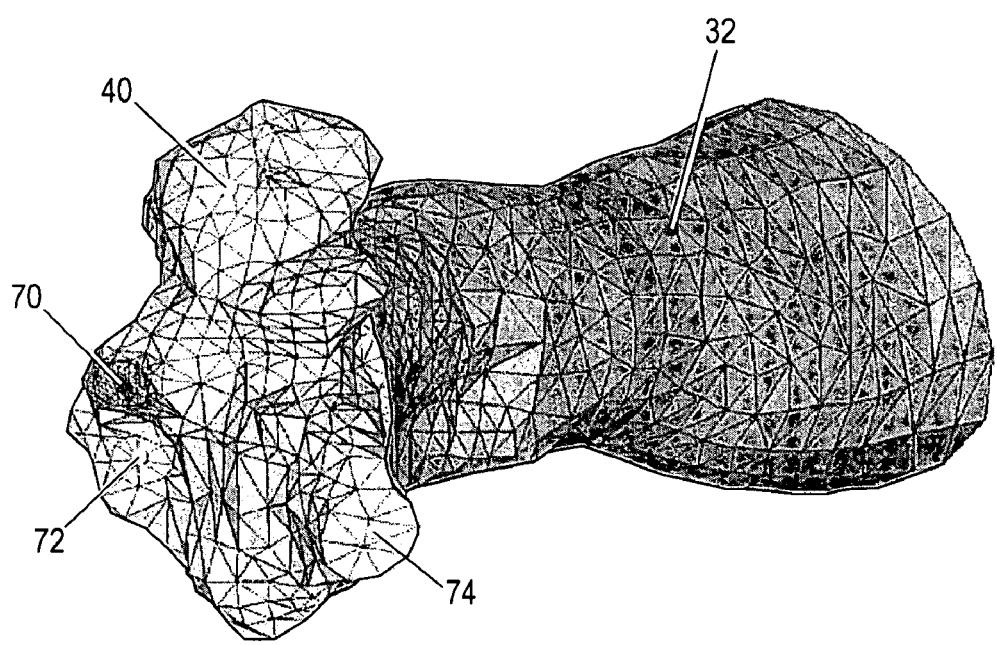
FIG. 4 shows a finite element model of the middle ear cavity and external ear canal in anterior-medial view where the locations of three cavity openings: oval window, round window, and Eustachian tube opening are displayed on the cavity wall.
Figure 10A:
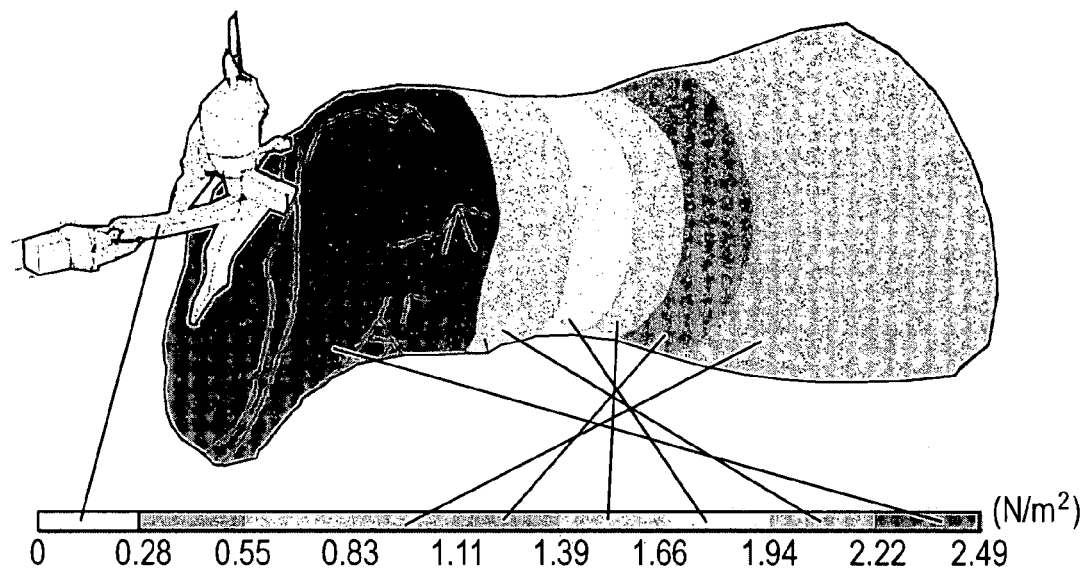
Figure 10B:
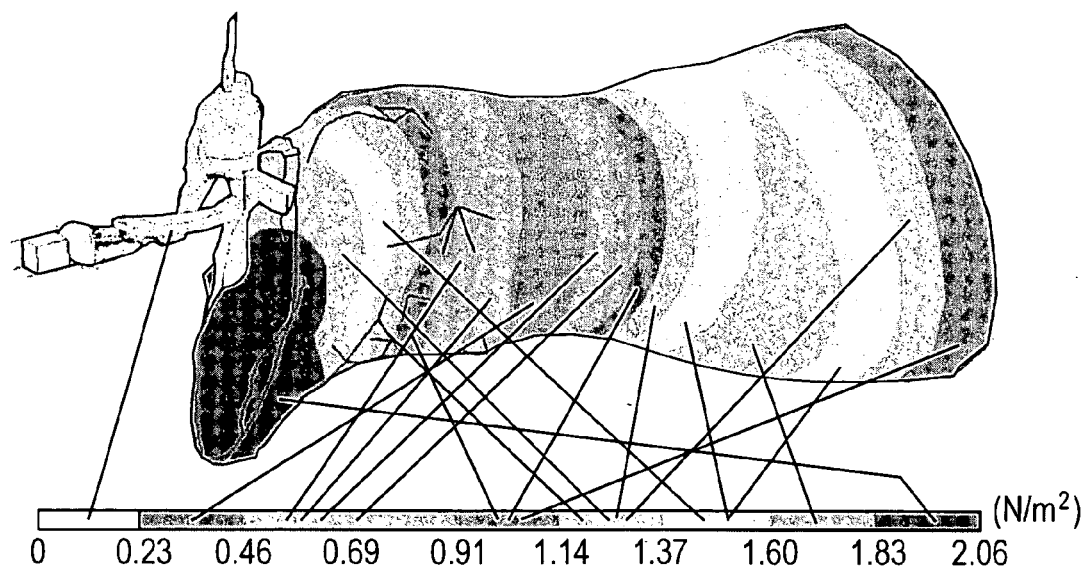

FIGS. 10A and 10 show acoustic pressure distribution in the ear canal predicted by the FE model at frequencies, namely FIG. 10A 4 KHz and FIG. 10B 8 KHz. With the sound pressure applied at the canal entrance of 90 dB SPL. The grey bands represent different pressure levels relative to the entrance pressure.

Figure 11A:
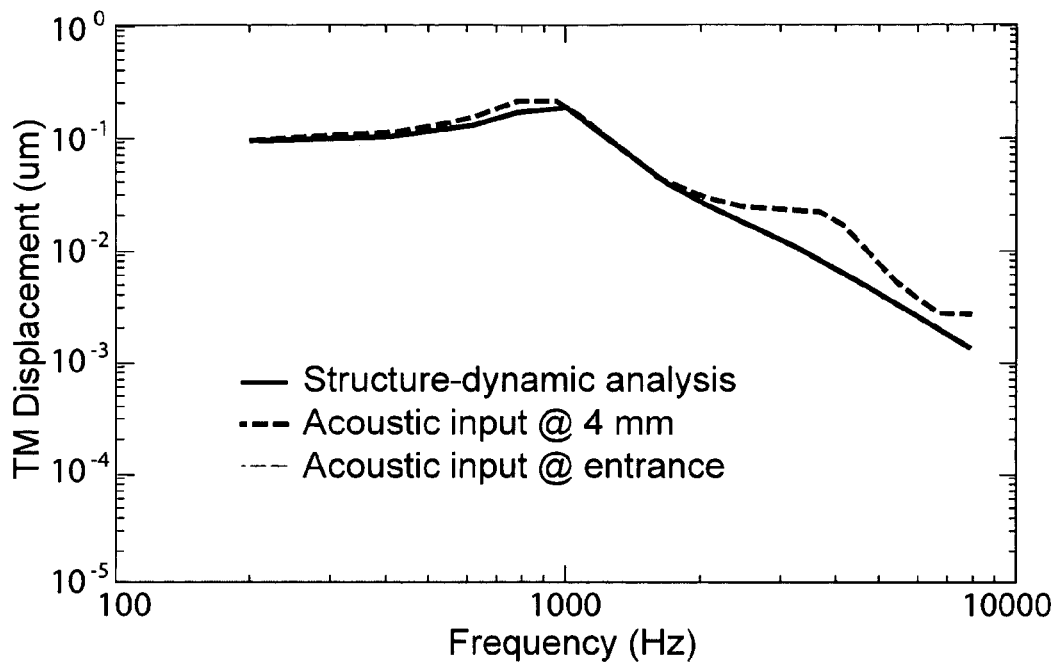
Figure 11B:
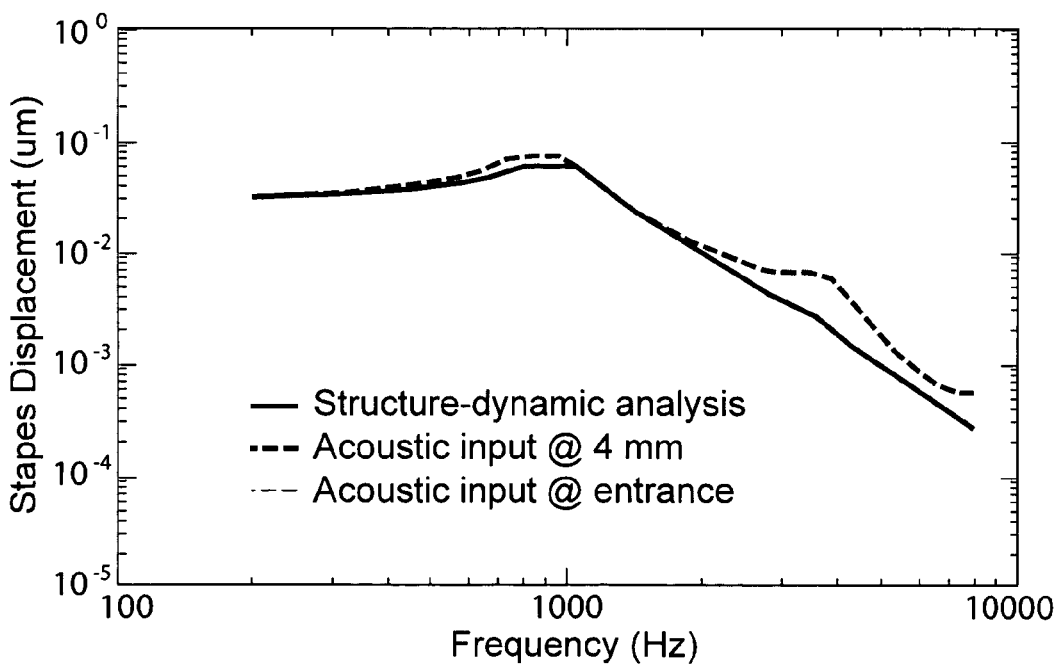

FIGS. 11A and 11B show a comparison of the FE model results obtained from acoustic-mechanical coupled analysis of the ear canal air column and middle ear ossicular structures. In particular, FIG. 11A shows the TM displacements predicted by the model in 3 cases: 90 dB SPL applied on the lateral surface of the TM, i.e., dynamic structural analysis (solid line), 90 dB input at 4 mm away from the TM (umbo) (thin broken line), and the same acoustic pressure input at the canal entrance (thick broken line); FIG. 11B shows the stapes footplate displacements predicted by the model in three same cases as shown in FIG. 11A.

Figure 12:
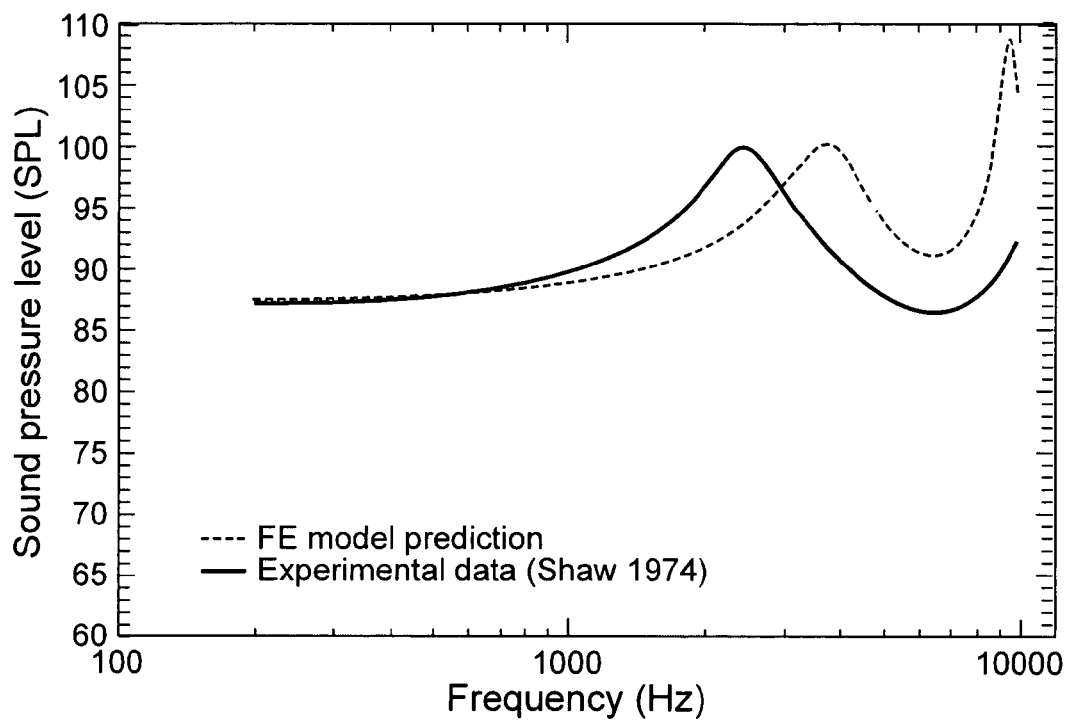

FIG. 12 shows a sound pressure level near the umbo inside the external ear canal when the harmonic sound pressure of 90 dB SPL was applied at the canal entrance. The broken line is the FE model-derived spectral curve and the solid line is the experimental measurement from Shaw[40].

Figure 13:
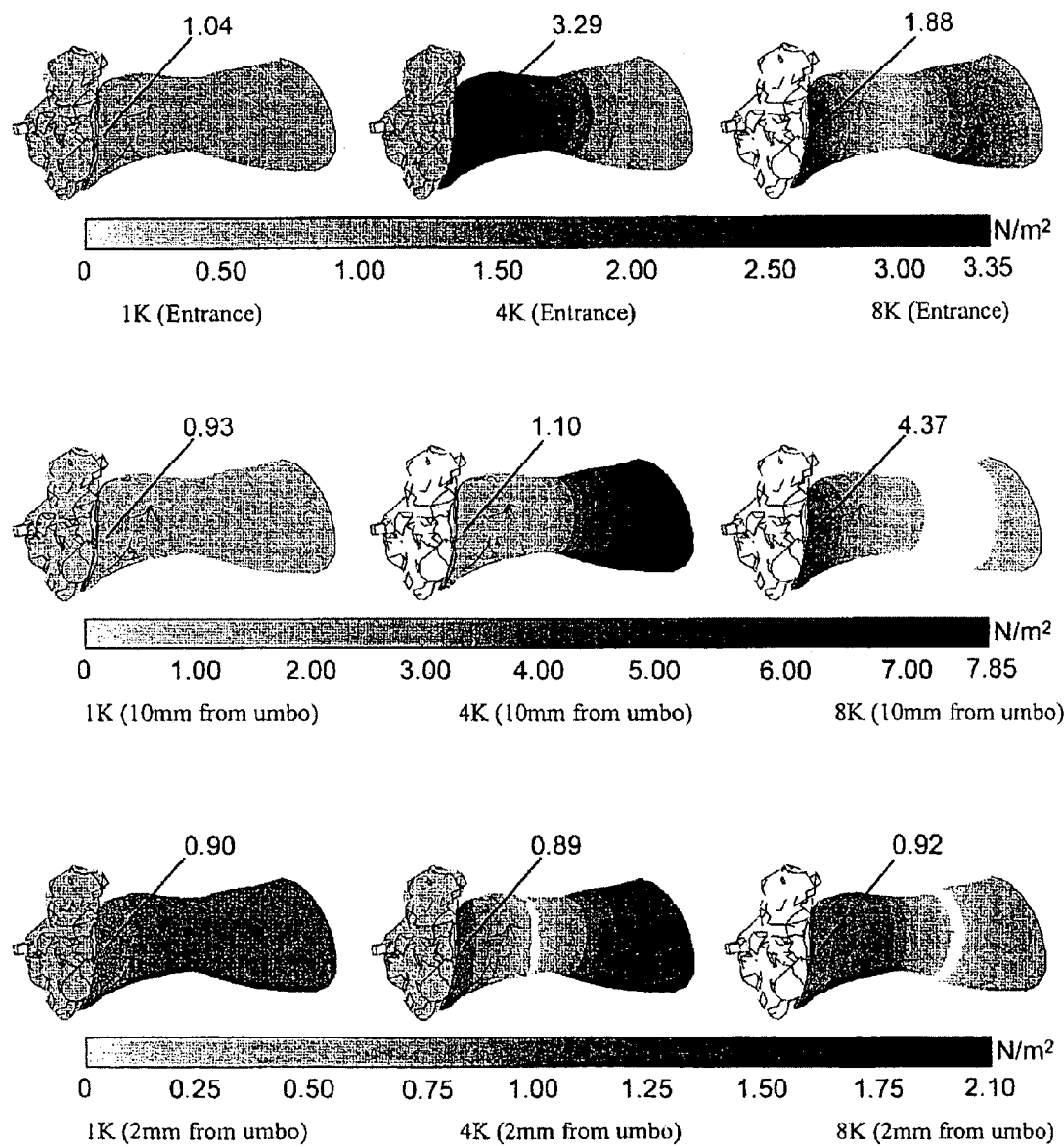

FIG. 13 shows anterior-medial views of acoustic pressure distributions in the ear canal and middle ear cavity at frequencies of 1, 4, and 8 kHz. The input sound pressure of 90 dB SPL was applied at the canal entrance (top row), 10 mm from the umbo (middle row), and 2 mm from the umbo (bottom row) in the canal. The numbers appearing in FIG. 13 indicate the acoustic pressure calculated at the lateral site of the TM.

Figure 14A:
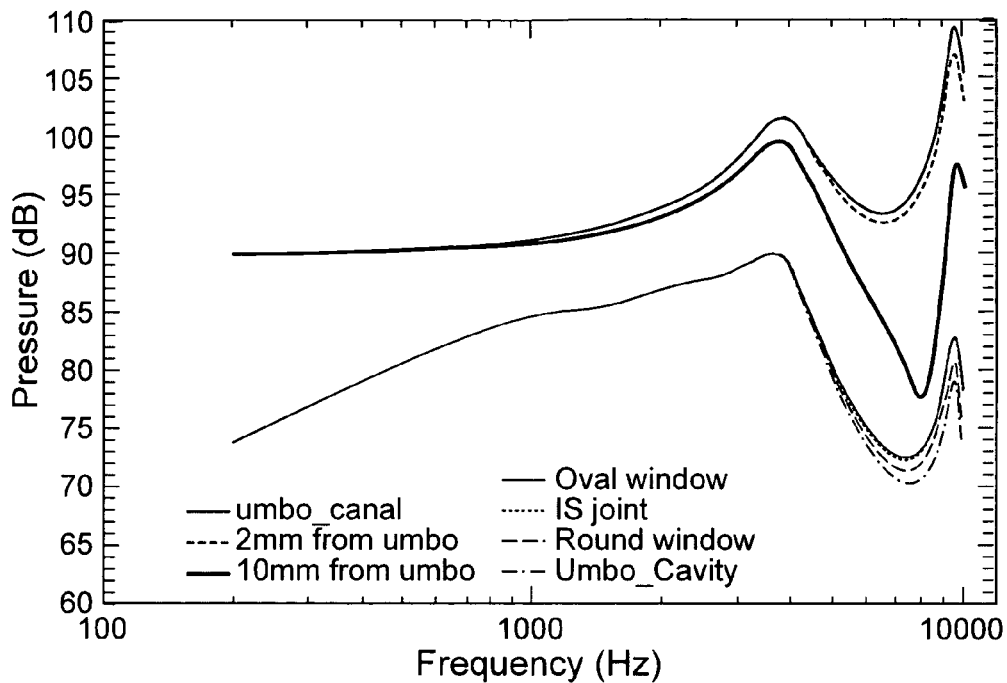
Figure 14B:
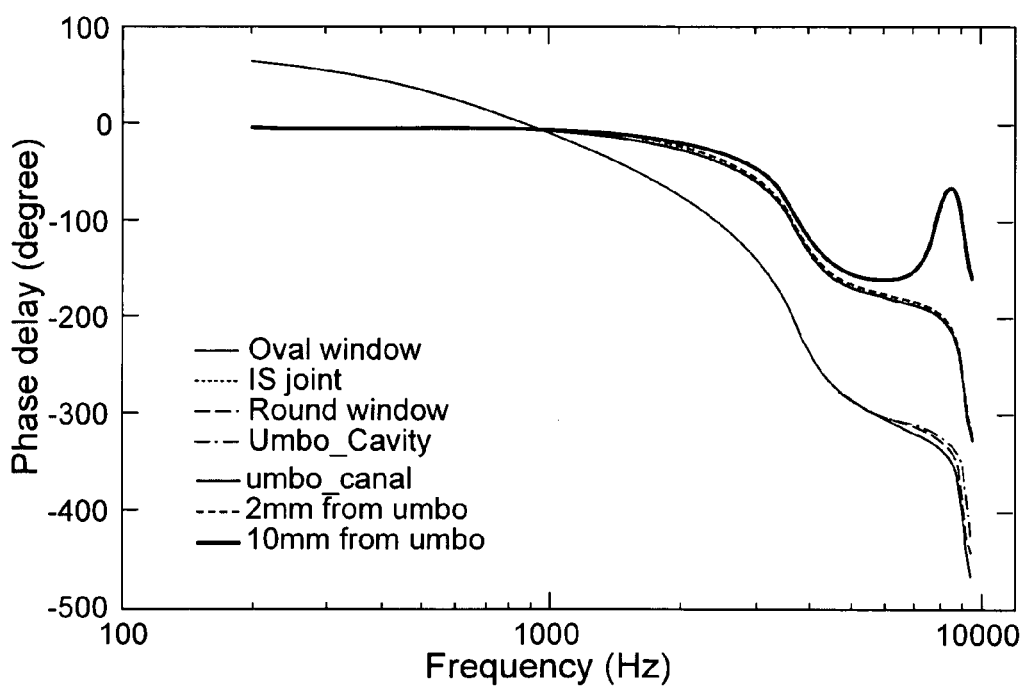

FIGS. 14A and 14B show FE frequency response curves of harmonic sound pressure in the canal (thick lines) and middle ear cavity (thin lines). The 90 dB SPL was input at the canal entrance. Namely, FIG. 14A displays the pressure magnitude and FIG. 14B the phase angle. Three thick lines represent the sound pressure at the umbo (solid), 2 mm from the umbo (dashed), and 10 mm from the umbo (solid-thick) in the canal. Four thin lines represent the sound pressure near the oval window or stapes footplate (solid), IS joint (dashed), round window (broken), and umbo (dash+point) inside the middle ear cavity.

Figure 15:
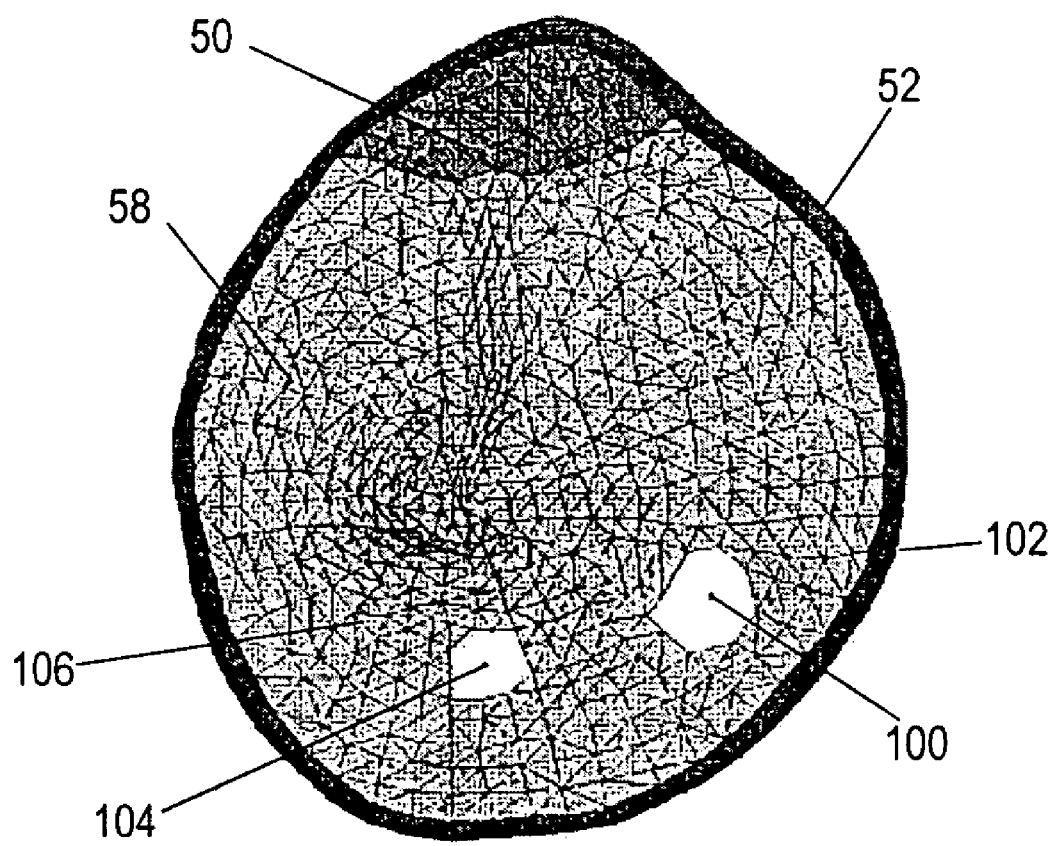

FIG. 15 shows a lateral view of the TM with two perforations: Case #1—the perforation located in the inferior-posterior site of the TM; Case #2—the perforation located in the inferior site.

Figure 16A:
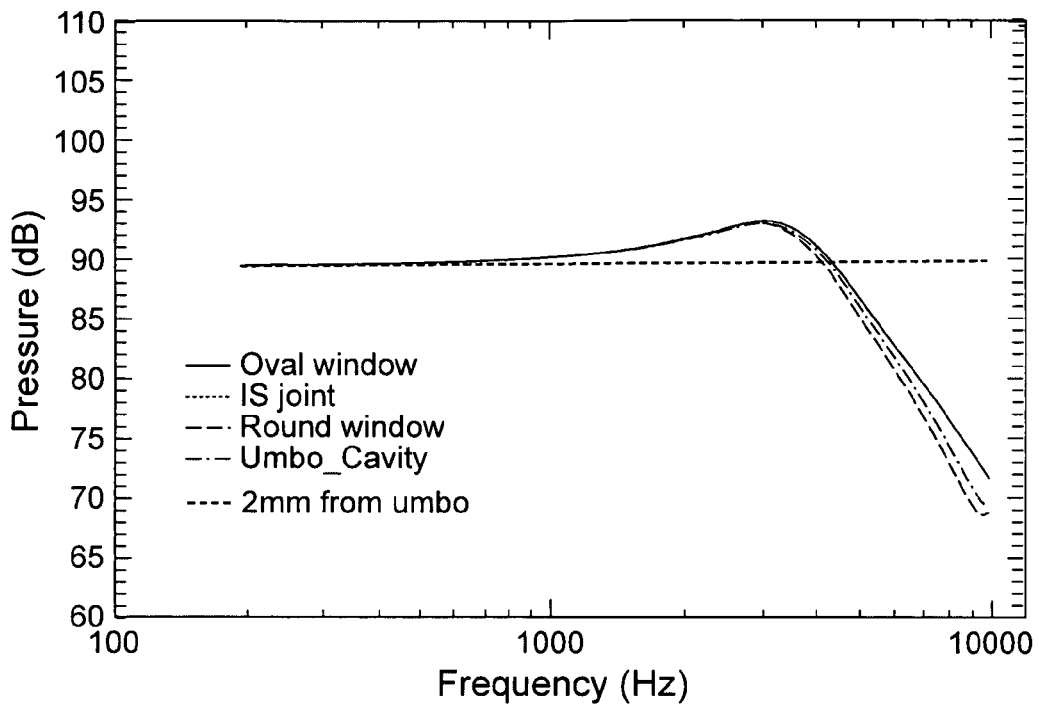
Figure 16B:
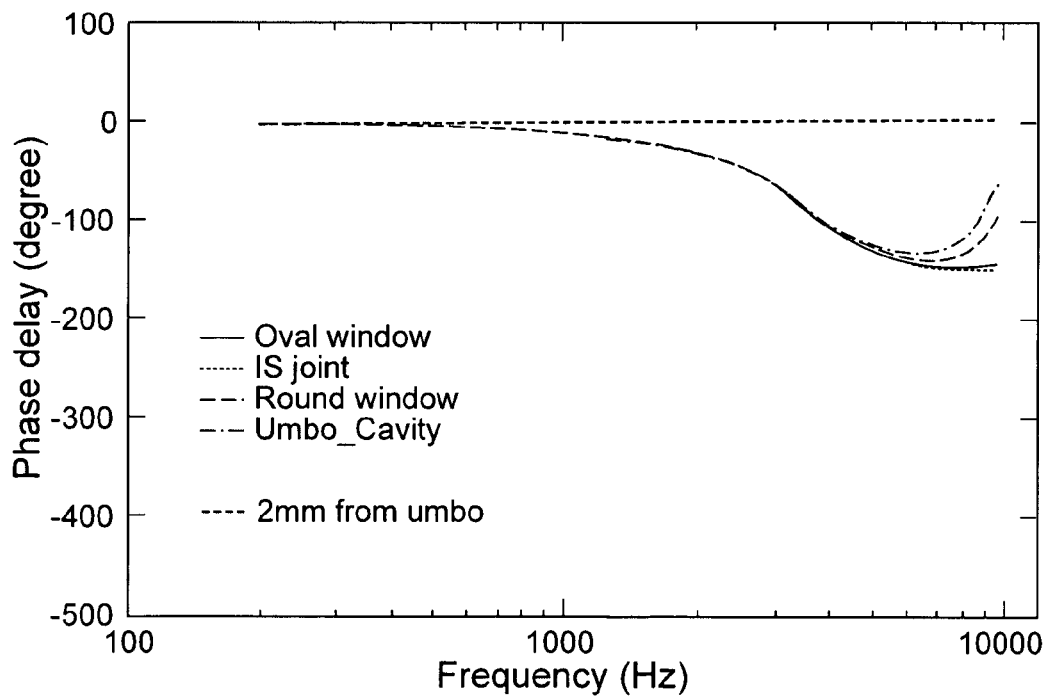

FIGS. 16A and 16B show FE frequency response curves of harmonic sound pressure at 4 locations inside middle ear cavity (thin lines) with perforation in the inferior-posterior site of the TM (Case #1): near the oval window or stapes footplate (solid), IS joint (dashed), round window (broken), and umbo (dash+point). The 90 dB SPL was applied at 2 mm from the umbo in the canal (thick dashed line). In particular, FIG. 16A displays the pressure magnitude and FIG. 16B the phase angle.

Figure 17A:
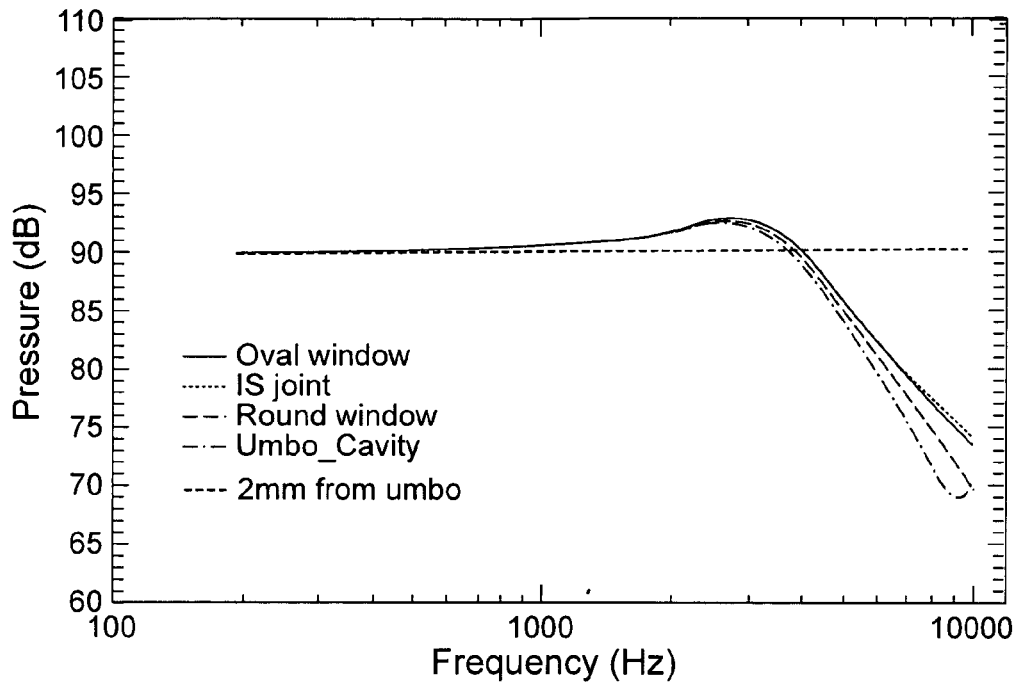
Figure 17B:
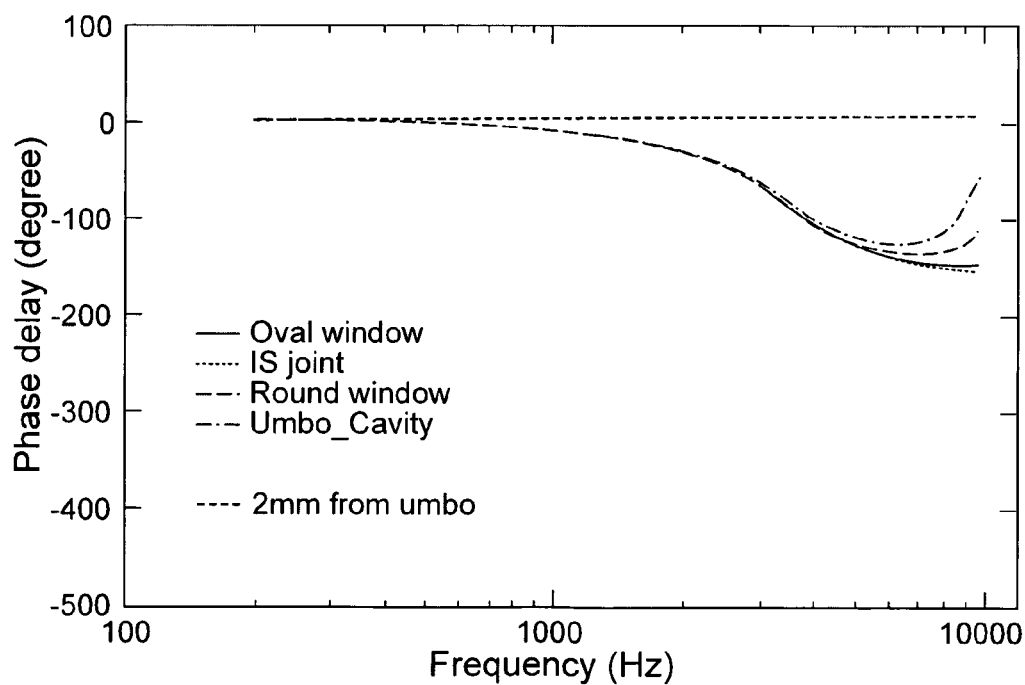

FIGS. 17A and 17B show FE frequency response curves of harmonic sound pressure at 4 locations inside middle ear cavity (thin lines) with perforation in the inferior site of the TM (Case #2): near the oval window or stapes footplate (solid), IS joint (dashed), round window (broken), and umbo (dash+point). The 90 dB SPL was applied at 2 mm from the umbo in the canal (thick dashed line). FIG. 17A displays the pressure magnitude and FIG. 17B the phase angle.

Figure 18A:
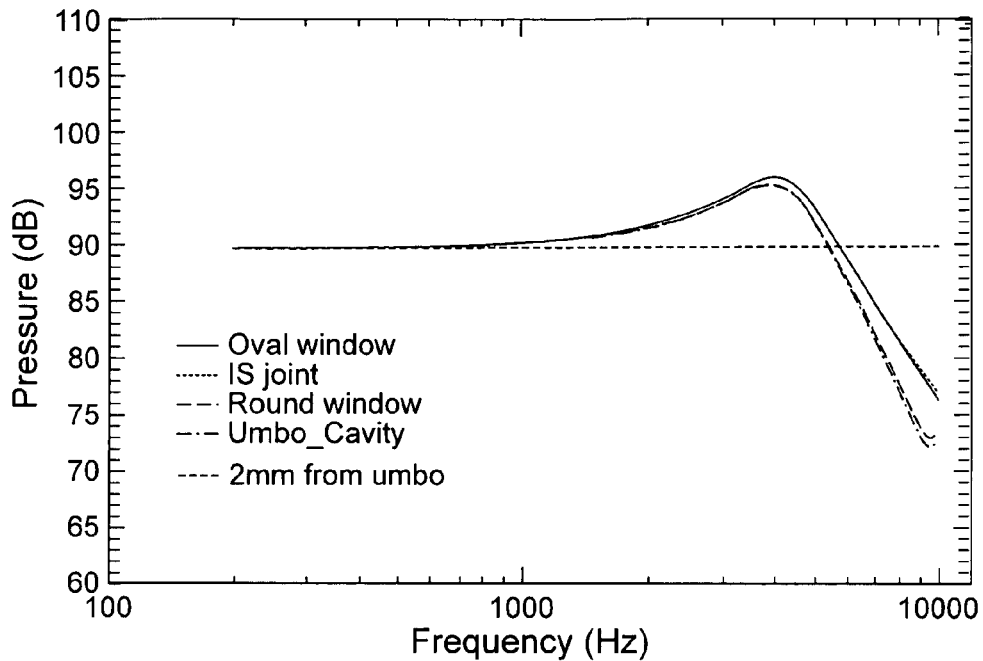
Figure 18B:
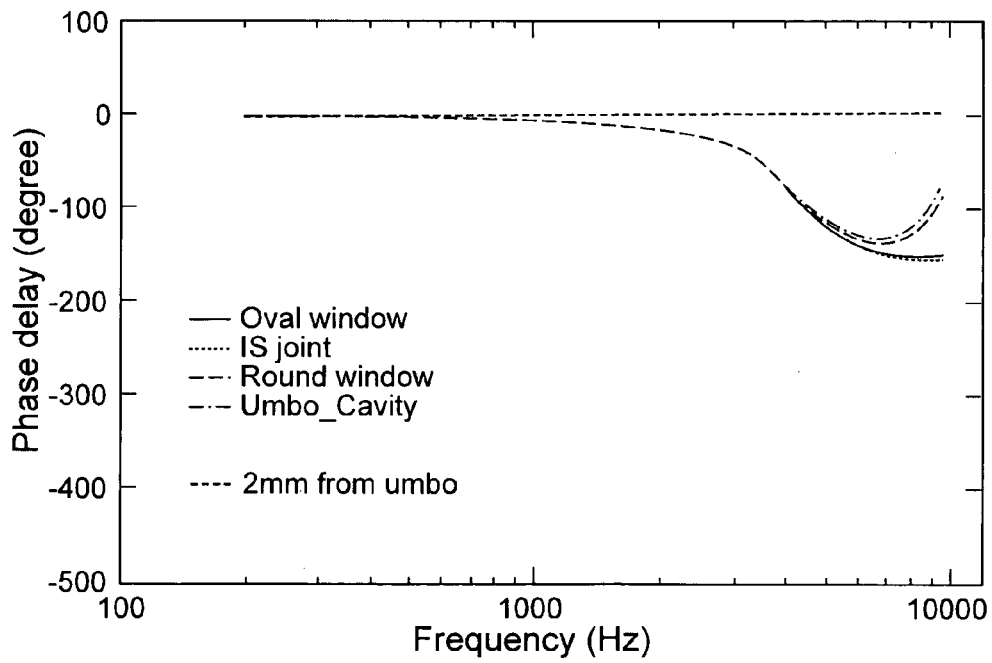

FIGS. 18A and 18B show FE frequency responses of the harmonic sound pressure at 4 locations inside middle ear cavity (thin lines) with combined perforations in both inferior-posterior and inferior sites of the TM: near the oval window or stapes footplate (solid), IS joint (dashed), round window (broken), and umbo (point+broken). The 90 dB SPL was applied at 2 mm from the umbo in the canal (thick dashed line). FIG. 18A displays the pressure magnitude and FIG. 18B the phase angle.

Figure 19A:
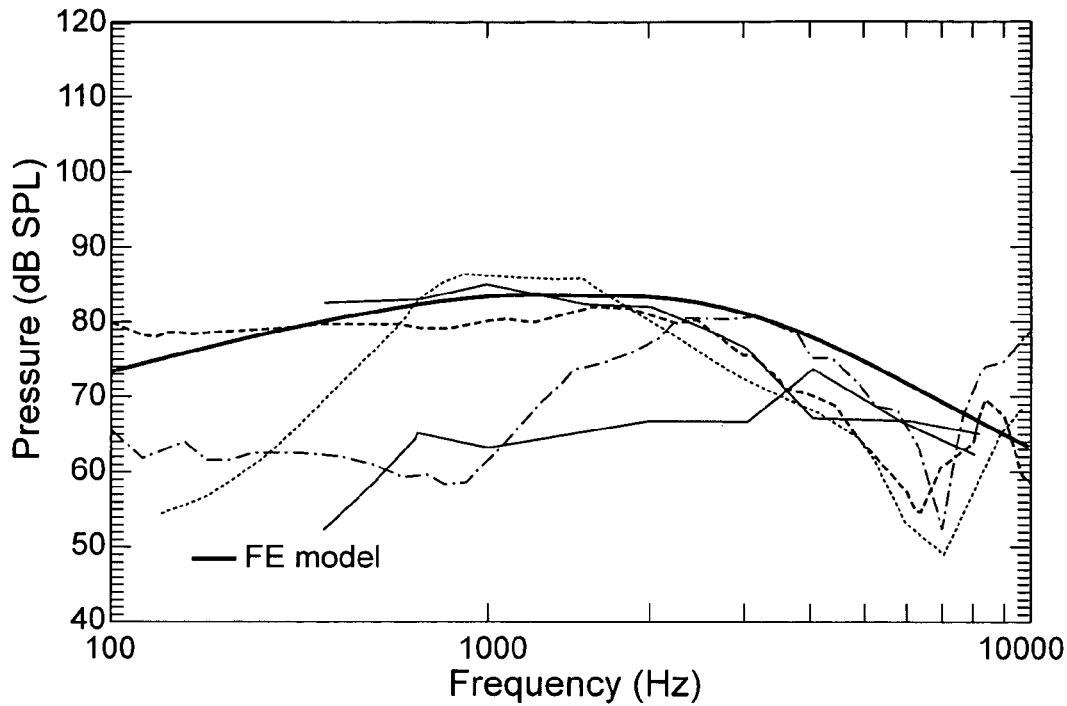
Figure 19B:
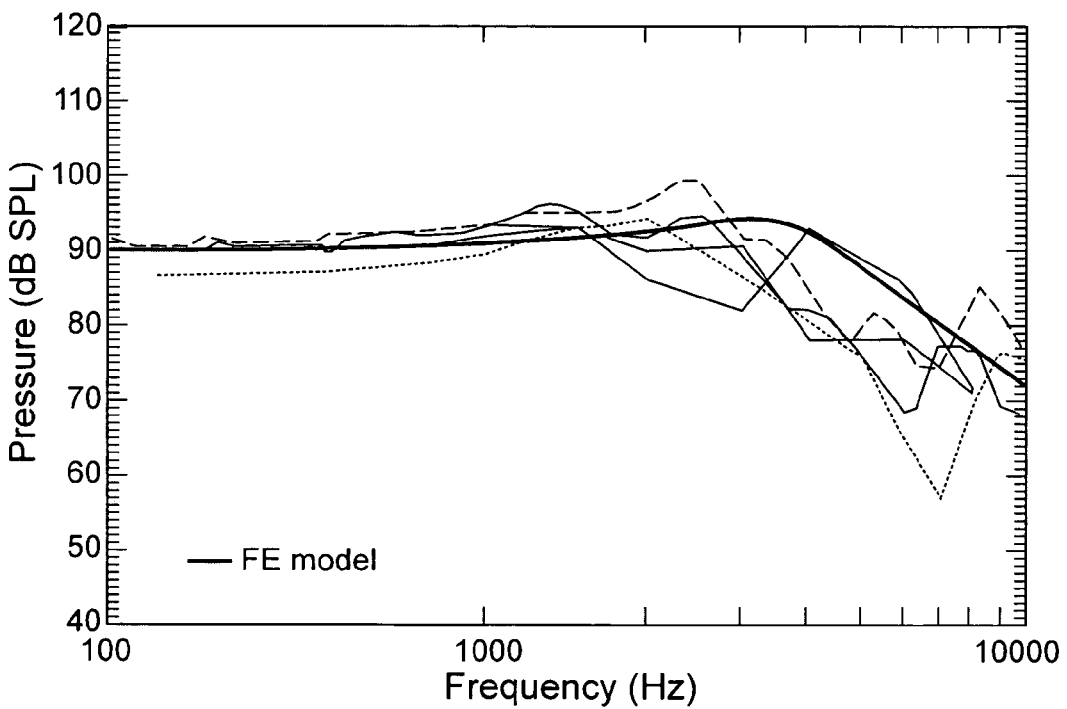
Figure 19C:
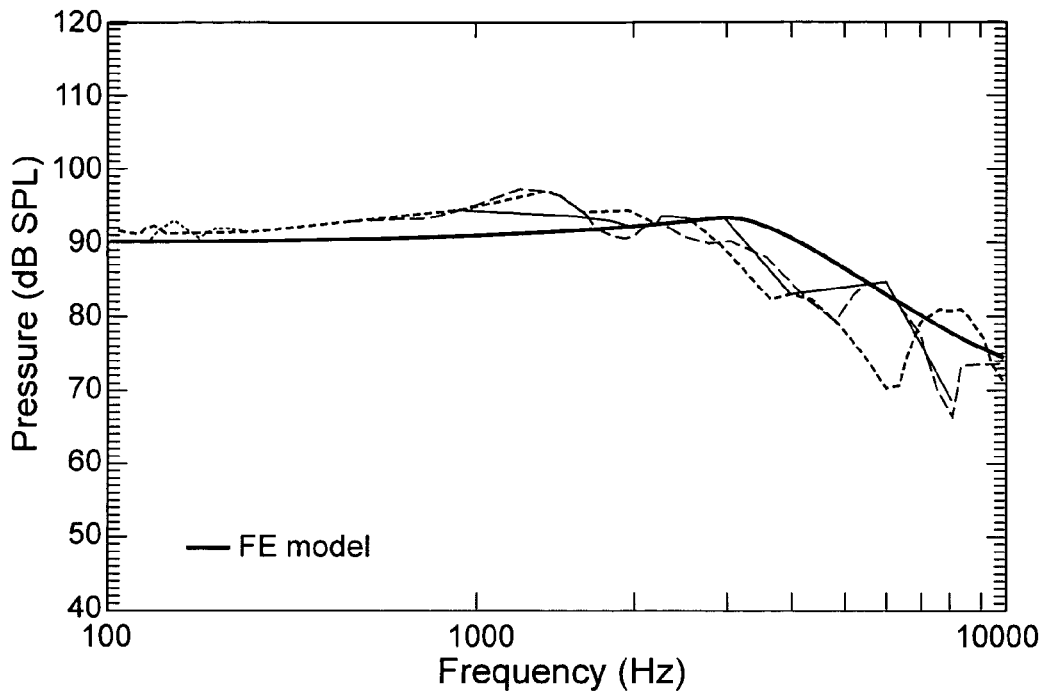
Figure 19D:
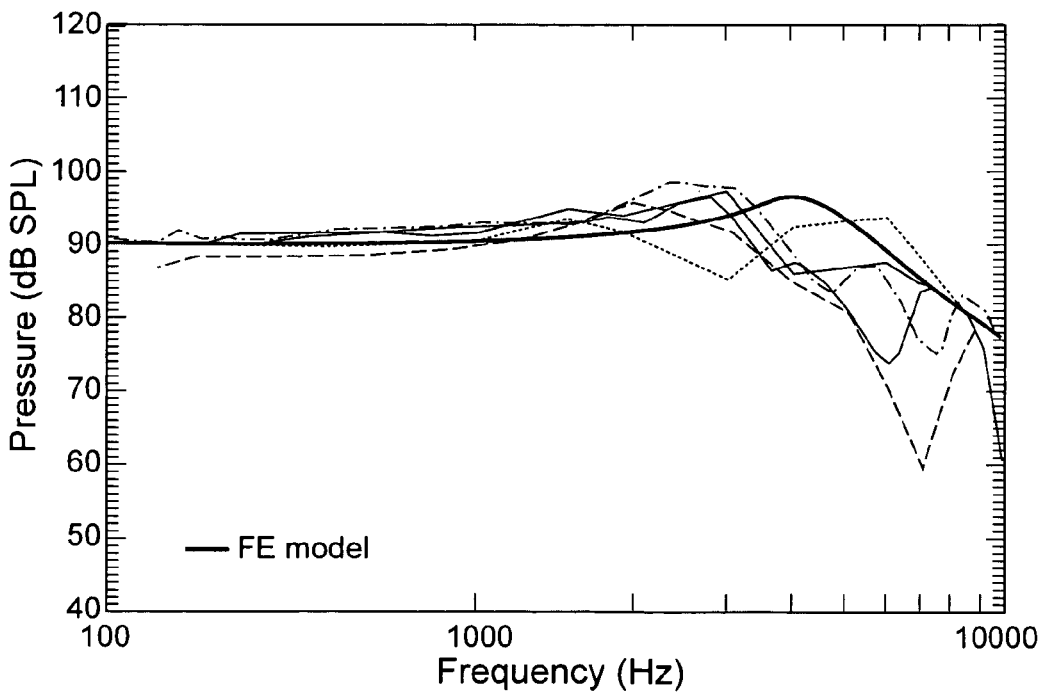

FIGS. 19A-D show the effect of the TM perforation on frequency responses of the sound pressure near the IS joint in the middle ear cavity: comparisons between FE results and the experimental data measured in 5 temporal bones. Namely, FIG. 19A shows the frequency responses for a normal TM; FIG. 19B shows the frequency response for a TM perforation in inferior-posterior site (Case #1); FIG. 19C shows the frequency responses for a TM perforation in inferior site (Case #2); and FIG. 19D shows the frequency responses for combined TM perforations in both inferior-posterior and inferior sites. In FIGS. 19A-D the thick solid line represents the FE results while others represent the temporal bone measurements.

Table 1 represents exemplary dimensions and physical properties of human ear finite element model (FE) in comparison with published data.

Table 2 represents exemplary material properties used for middle ear structures of the FE model.

Table 3 represents exemplary boundary conditions of one version of a human ear FE model.

Table 1A represents exemplary material properties used for another version of the FE model.

Table 2A represents exemplary structural boundary conditions for the FE model.

DETAILED DESCRIPTION OF THE INVENTION

Presently preferred embodiments of the invention are shown in the above-identified figures and described in detail below. In describing the preferred embodiments, like or identical reference numerals are used to identify common or similar elements. The figures are not necessarily to scale and certain features and certain views of the figures may be shown exaggerated in scale or in schematic in the interest of clarity and conciseness.

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort, even if complex and time-consuming, would be a routine undertaking for those of ordinary skill in the art having the benefit of this disclosure. The following detailed description is organized into Section A describing a "'One-Chamber' Analysis and Model", and Section B describing a "'Two-Chamber' Analysis and Model." The "one-chamber" (e.g., ear canal) acoustic-structural coupled FE analysis is conducted within one chamber and the surrounding boundaries, e.g., the following description describes research conducted between the external ear canal air column and the TM. The "two-chamber" acoustic-structural coupled analysis describes an acoustic-structural-acoustic coupling effect of the ear, such as the ear canal (one-chamber)—TM and ossicles (structural)-middle ear cavity (second chamber).

A. "One-Chamber" Analysis and Model

Method

I. Construction of Geometric Model

Figure 1:
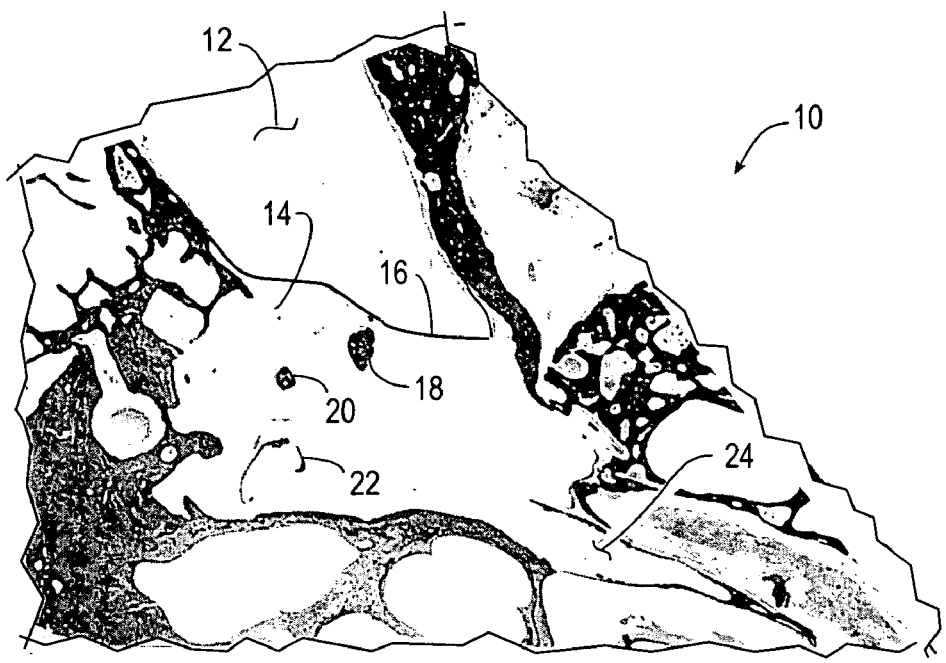
FIG. 1 shows a typical histological section image of a human temporal bone.

An extracted fresh human temporal bone (male, age 61, left ear), obtained through the Willed Body Program at the University of Oklahoma Health Sciences Center, was visually inspected using an operating microscope to confirm an intact TM 50 and 58 (50: pars flaccida of the tympanic membrane; 58: pars tensa of the tympanic membrane) and normal ear canal. Then, 780 histological sections of 20 μm thickness were prepared from this temporal bone and scanned into a computer such as a PC or a mainframe as section images (FIG. 1). An exemplary section image 10 is shown in FIG. 1 and forms a part of an ear canal 12, a middle ear cavity 14, an eardrum 16, a malleus 18, an incus 20, a stapes 22, and a Eustachian tube 24. The images were segmented to construct a 3-D geometric model of the ear. Complete details can be found in a previous publication.[7,25] Briefly, all histological sections were scanned into the computer with 1200 pixel/inch resolution although the resolution can vary. The images were aligned with a template constructed from a typical section image using the fiducial marks on each section. The aligned images were then trimmed as standard-sized images and brought onto a sketch plane in CAD software, SolidWorks (SolidWorks, Inc., Concord, Mass.). The aligned and treated images were then digitized by marking points along the outlines of the middle ear structures identified by the otologic surgeon. These structures included the tympanic membrane, ossicles, attached ligaments and muscle/tendons, middle ear cavity wall, and external ear canal wall. Finally, the images were segmented to a 3-D CAD model of the human ear.

Characteristic dimensions of the middle ear components were measured from the geometric model and compared with the published anatomical data and the data of the inventor's previous middle ear model (Table 1). The results show that most dimensions of the present model are within the range of published anatomical data, but some of them are different from the inventor's previous model. The diameters and surface area of the TM 50 and 58 and the total length of the malleus in the present model, for instance, are greater than those of the inventor's previous model. The difference reflects the individual variation of temporal bones.

II. Finite Element Modeling

Finite Element Mesh

Figure 2:
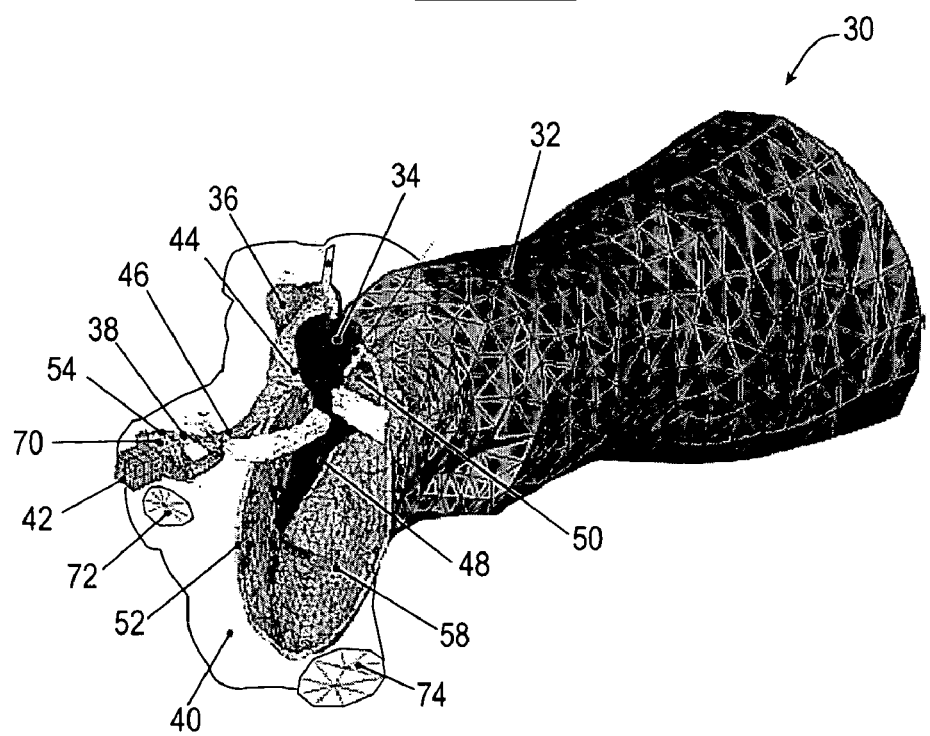
FIG. 2 shows a finite element model of a human left ear including tympanic membrane, three ossicles (malleus, incus, and stapes), two joints and manubrium, ligaments and muscles/tendons (C1, C2, C3, C4, C5, C7), tympanic annulus, stapedial annular ligament, external ear canal, middle ear cavity, and cochlear load, in anterior-medial view.

The geometric models of the ear structures were imported into a computer program for geometric reconstruction and finite element meshing, such as HyperMesh (Altair Computing, Inc., Troy, Mich.), to generate the FE mesh and apply boundary conditions. Hypermesh runs on a personal computer, such as a Dell Dimensions 4100. The meshing process was extremely time-consuming and it was difficult to refine the mesh for such a complicated system. Therefore, we first determined the appropriate mesh density for the system by testing the effect of mesh refinement of a simple cantilever beam or a circular plate. FIG. 2 shows a FE model 30 of a human left ear including an external ear canal 32, middle ear ossicles (malleus 34, incus 36, and stapes 38) with attached ligaments tendons C1-C5 and C7 middle ear cavity 40, and cochlear load 42 in anterior-medial view. The middle ear cavity 40 is displayed transparently. The TM 50 and 58 was meshed by 3-noded shell elements with a total of 1,123 elements and the ossicular bones were meshed by 4-noded tetrahedral solid elements with a total of 6,663 elements. An incudomalleolar joint, 44 incudostapedial joint, 46 and manubrium 48 that connects a malleus handle to a tympanic membrane 50 and 58 were meshed by 4-noded solid elements at a total of 655 elements, although other types and numbers of elements can be used.

The boundaries of the middle ear structural vibration system consist of a tympanic annulus 52, middle ear suspensory ligaments, tendons or muscles C1-C5 and C7, stapedius annular ligament 54, and cochlear load. The plurality of suspensory ligaments and muscle tendons were assumed as elastic constraints. For example, four major suspensory ligaments (superior malleus and incus C1, lateral malleus C2, posterior incus C3, and anterior malleus C4) and two intra-aural muscle tendons (stapedial muscle C5 and tensor tympani muscle C7) were assumed as elastic constraints with 4-noded solid elements. The tympanic annulus 52 was modeled as elastic supports of the tympanic membrane 50 and 58 with 3-noded shell elements. A stapedial annular ligament was modeled by 25 linear spring elements distributed evenly around the periphery of the footplate. The effect of cochlear fluid on acoustic-mechanical transmission through the ossicular chain was modeled as a mass block with 10 dashpots (5 on each side) attached between the stapes footplate and fixed bony wall, which represented distributed damping dominant impedance. This assumption was based on the experimental studies of cochlear impedance on human temporal bones[1,20] and the circuit model calculation for effective mass of cochlear fluid.[17,18,31] The cochlear impedance defined as the pressure per unit volume velocity of stapes footplate varied between 12 and 25 GΩ at the frequency of 0.5-5 kHz was reported by Aibara et al.[1] The value of 20 GΩ cochlear impedance applied on 3.2 mm$^2$ of stapes footplate was used to calculate the dashpot damping, which resulted in 10 dashpots (5 on each side) with damping coefficient of 0.02 Ns/m each.

Figure 3:
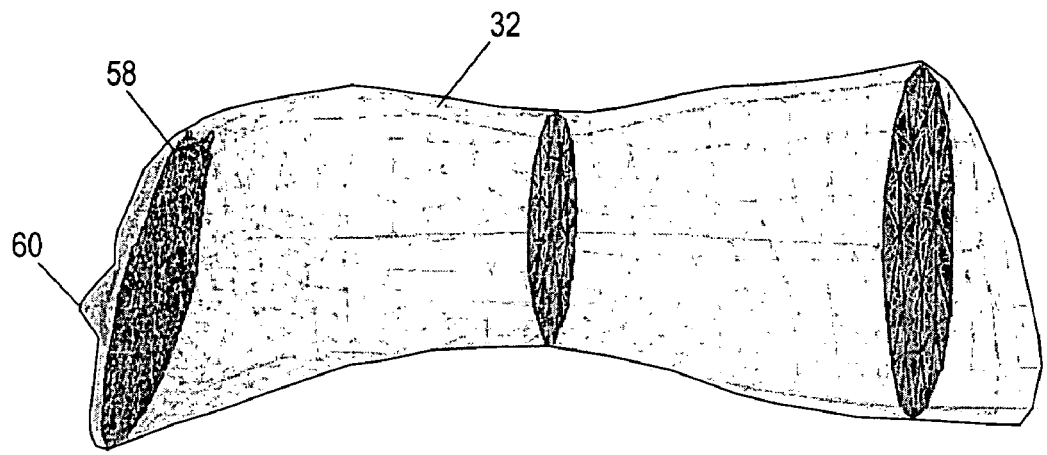
FIG. 3 shows another example of a finite element model of the external ear canal. Three sections shown in the figure were used for calculating the change of cross-sectional area along the canal axis.

The air in the external ear canal 32 and middle ear cavity 40, which enclosed the air volume of 1,657 and 455 mm$^3$, respectively, were meshed with 4-noded acoustic elements. FIG. 3 shows the ear canal 32 with the eardrum 50 and 58 attached in anterior view. The length of the canal 32 from an umbo 60 to the entry section along the canal axis was 30.22 mm. The canal length superiorly was 25.18 mm and the length inferiorly was 31.9 mm. The cross-sectional area varied from 75.53 mm$^2$ (near the TM 50 and 58) to 45.32 mm$^2$ (the most narrow portion) to 90.13 mm$^2$ at the canal entrance as shown in FIG. 3. The angle between the eardrum basal plane and ear canal axis was about 57°. The published anatomical data for the external ear canal 32 include the average horizontal diameter 6.5 mm, mean vertical diameter 9 mm, length posterosuperiorly 25 mm, and length inferoanteriorly 31 mm.[4,30] Based on these data, the canal air column volume would range from 830 and 1,972 mm$^3$. The canal volume (1,657 mm$^3$) calculated from the model is within the published range.

FIG. 4 shows anterior-medial view of the middle ear cavity 40 and ear canal 32. The locations of an oval window 70 where a stapes footplate was seated, a round window 72, and an Eustachian tube opening 74 are displayed in FIG. 4. The areas of the oval window 70, round window 72, and Eustachian tube opening 74 were measured as 2.05, 7.32, and 3.97 mm$^2$ from the model, respectively.

Material Properties

The human middle ear has been described as a linear system under the regular sound intensity of the hearing level for acoustic-mechanical transmission from the eardrum 50 and 58 to cochlea.[6,26] Thus, the materials of the middle ear system were assumed to be linear elastic. The Poisson's ratio was assumed 0.3 for the system based on the fact that all published Poisson's ratios of middle ear components were close to this value. Considering the complexity of biological system and lack of measurement in damping properties, the Raleigh damping parameters α and β for all materials of the middle ear system were assumed to be α=0s$^{-1}$, β=0.75×10$^{-4}$s. Material properties of the ossicles 34, 36, 38, TM 50 and 58, joints 44, 46, and manubrium 48 were obtained from published data or those used for a previous model (Table 2). The TM 50 and 58 was assumed as orthotropic material having a radial Young's modulus of 35 MPa in the pars tensa 58 and 10 MPa in the pars flaccida 50, and circumferential Young's modulus of 20 MPa in the pars tensa 58 and 10 MPa in the pars flaccida 50.

Material properties for the tympanic annulus 52, middle ear suspensory ligaments or muscle tendons C1-C5 and C7, and stapedial annular ligament 54 were first selected from limited published or assumed data from the sources listed in Table 3. The Young's modulus values were then finalized through cross-calibration, a process for determining undetermined model parameters. The Young's moduli of the superior mallear ligament C1, lateral mallear ligament C2, and tensor tympani tendon C7 were determined and finalized by the cross-calibration method. Briefly, by selecting appropriate, as yet, undetermined parameters of the model, the difference of the stapes footplate displacements was minimized between the FE model and the experimental data obtained from 17 bones at the input sound pressure of 90 dB SPL on the TM 50 and 58 in the ear canal.[6]

Table 3 lists Young's modulus or spring stiffness constant used for suspensory ligaments (C1-C5, and C7), tympanic annulus 52, and stapedial annular ligament 54 in the FE model. Compared with material properties used for boundary conditions in the inventor's group's previous middle ear model, the Young's moduli for suspensory ligaments C1-C5 and C7 were increased by an order of 10 in this model, following the cross-calibration process, which may reflect the individual variation of temporal bones. The tympanic annulus 52 was assumed the same value of $6.0 \times 10^5$ $Nm^{-2}$ as that used in previous model. There were no spring constraints on the plane of stapes footplate in this model and the spring constant for stapedial annular ligament 54 was determined to 40 $Nm^{-1}$ per spring through the cross-calibration process. The intact cochlear impedance was considered as viscous damping (dashpots) with a mass block of 25.5 mg that was calculated from the volume of cochlear fluid and the published cochlear impedance by Aibara et al.[1] and Rosowski et al.[24] The damping coefficient used for 10 dashpots in this study was assumed to be 0.02 $Nsm^{-1}$ for each dashpot based on calculation of the cochlea damping impedance 20 GΩ and the area of stapes footplate 3.2 $mm^2$.

FE Analysis

Analysis for sound transmission in the ear involves solid structure (e.g., soft tissues, bones), acoustics (e.g., air in the ear canal and middle ear cavity), and fluid (cochlear fluid), which belong to different engineering disciplines and result in different boundary conditions, element attributes and model parameters. FE analysis for structure, acoustic and fluid behavior is usually carried out independently. However, the ear as a complex system including the external ear canal 32, eardrum 50 and 58, ossicular bones 34, 36, 38 and joints 44, and 46, suspensory ligaments, C1-C5 and C7 and middle ear cavity 40, requires multi-field coupled FE analysis.

In this study, the investigation for functions of the ear was conducted using a two-step scheme. First, the structural analysis was employed to adjust and validate the FE model, and to study mechanical functions of the middle ear. When harmonic sound pressure was applied on the TM 50 and 58 from the ear canal side, the movement responses at different locations of the middle ear system were calculated through the FE structural analysis. Second, the acoustic-structural coupled analysis was employed to investigate the acoustic effect on mechanical vibration transmission in the ear using the validated FE model. As a preliminary study on acoustic effect, the acoustic-mechanical coupled analysis was only involved between the external ear canal air and middle ear ossicular structure. This ear canal-TM 50 and 58 coupling or "one-chamber" acoustic-mechanical study aimed to finally perform the multi-field FE analysis of the entire ear.

We made the following assumptions for the air in the canal: 1) compressible, 2) inviscid, and 3) uniform mean density and pressure. The governing equation for the air in the canal was the wave equation for acoustics:

$$\frac{1}{c^2} \frac{\partial^2 P}{\partial t^2} - \nabla^2 P = 0 \qquad (1)$$

where P is acoustic pressure, c is speed of sound and $c=\sqrt{k/\rho_o}$ in fluid medium, $\rho_o$ is mean fluid density, k is bulk modulus of fluid, and t is time. Considering the fluid-structure interface (e.g., the lateral surface of the TM 50 and 58) where the pressure gradient of the air is related to the normal acceleration of the structure by the fluid momentum equations, the discretized wave equation can be strongly coupled with the discretized structural equation.[3] Thus, coupling is handled by calculating element matrices or element load vectors that contain all necessary degrees of freedom. In this "one-chamber" acoustic-mechanical study, the speed of the sound and density of the air were assumed as 334 $ms^{-1}$ and 1.29 $kgm^{-3}$, respectively. The surface of acoustic elements next to the canal wall were defined as "impedance surface", assigned with specific sound absorption coefficient μ(μ=1 for full sound absorption). The lateral surface of the TM 50 and 58 was defined as fluid-structural interface (FSI) where the acoustic pressure distribution was coupled into the structural analysis as the force input in ANSYS (ANSYS Inc., Canonsburg, Pa.) operated in a computer, such as a Dell Dimensions 4100 personal computer.

Results

I. Validation of the FE Model

The FE model was first tested and validated by comparing the responses of the middle ear system to harmonic pressure on the lateral surface of the TM 50 and 58 between the FE analysis and published experimental measurements. When a simulation of uniform pressure of 90 dB SPL (0.632 Pa, rms value) was applied on the lateral side of the TM 50 and 58, the harmonic analysis was conducted on the model over the frequency range of 200-8000 Hz using ANSYS. The magnitudes of the displacements at the TM 50 and 58 and stapes footplate were calculated and projected to the piston-like direction, i.e., the direction perpendicular to the footplate. The published TM 50 and 58 and stapes footplate displacements were all obtained along the piston-like direction using laser Doppler vibrometers.

FIG. 5A shows the FE model-derived frequency response curve of the TM 50 and 58 displacement in comparison with the corresponding curves obtained from ten temporal bones at the same input sound pressure level of 90 dB applied on the TM 50 and 58 in the ear canal. The model-derived frequency response curve of the stapes footplate displacement is displayed in FIG. 5B, in comparison with the experimental data measured from the same ten bones using the double laser interferometers. This figure shows that the FE model-predicted TM 50 and 58 and stapes footplate curves fall into the range of the 10 temporal bone experimental curves across the frequency range of 250 to 8000 Hz.[8]

The dynamic behavior of the ear for sound transmission can be characterized as the stapes displacement transfer function (S-DTF), the ratio of the displacement at the stapes footplate (out port of the middle ear) to the sound pressure applied on the TM 50 and 58 in the ear canal side. Alternatively, the ratio of the TM 50 and 58 displacement to the ear canal sound pressure is defined as the TM 50 and 58 displacement transfer function (TM-DTF), which represents the middle ear transfer function at the TM 50 and 58 (input port of the middle ear system). FIG. 6A shows the S-DTF magnitude predicted by the FE model (thick solid line), compared with the mean data measured in ten temporal bones (thick broken line) and the published data from Kringlebotn and Gundersen[16] and Aibara et al.[1] The S-DTF predicted by the inventor's previous middle ear model is also included in FIG. 6A (thin solid line). FIG. 6B shows the TM-DTF magnitude derived from the FE model (thick solid line) and compared with the mean data (thin broken line) reported by Goode et al.[10] and the results obtained from ten bones in this study (thick broken line). The TM-DTF measured in 64 normal human subjects published by Nishihara and Goode[21] is also included in FIG. 6B with the upper and lower limits of 64 experimental curves. All comparisons with the experimental data measured in human temporal bones or human subjects shown in FIGS. 6A and 6B indicate that the FE model was well predicting middle ear mechanical sound transmission. Compared with the inventor's previous model, the present FE model provides more accurate predictions on transfer function of the middle ear. Thus, the FE model is suitable to study the dynamic behaviors of normal or pathological middle ear.

II. Otological Applications of the FE Model

Change of TM Thickness or Stiffness

Effects of TM 50 and 58 thickness or stiffness change on stapes footplate and TM 50 and 58 movements were tested using the validated FE model of human ear. FIG. 7A shows the footplate displacement induced by 90 dB sound pressure on the lateral side of the TM 50 and 58 when average thickness (h) of the TM 50 and 58 was changed from 0.05 to 0.2 mm. The normal thickness used for FE model in this study was 0.074 mm (solid line in FIG. 7A). As membrane thickness was increased, the footplate displacement was reduced, especially at low frequencies ($f \leq 1$ KHz). There was no pronounced change of the displacement when TM 50 and 58 thickness varied from 0.05 to 0.1 mm. The similar results were observed from the model-predicted TM 50 and 58 displacement curves (data not shown here). The results in FIG. 7A suggest that the thickened TM 50 and 58, which usually occurs after surgical treatment of tympanic membrane perforation, has detrimental effect on movement of the stapes footplate.

FIG. 7B shows the frequency response curves of stapes footplate displacement in response to TM 50 and 58 stiffness changes. The solid line represents the normal Young's modulus of $(3.5, 2.0) \times 10^7$ Nm$^{-2}$ at pars tensa and $(1.0, 1.0) \times 10^7$ Nm$^{-2}$ at pars flaccida. The first number in parentheses represents radial Young's modulus and the second number the circumferential modulus. The thick and thin broken lines represent a decrease or increase in Young's modulus by a factor of 10 in both pars tensa 58 and pars flaccida 50. As can be seen in FIG. 7B, the frequency response of stapes footplate displacement is very sensitive to the TM 50 and 58 stiffness. The increased stiffness (thin broken line) resulted in reduced stapes displacements at low frequencies ($f < 1.5$ KHz) and increased displacements at high frequencies ($f \geq 1.5$ KHz). These results agree with the inventor's previous model prediction on the effect of TM 50 and 58 stiffness on stapes displacement.[7] The decrease of stiffness (thick broken line) resulted in slightly increased displacements at very low frequencies ($f < 500$ Hz) and significantly decreased displacements at high frequencies ($f \geq 500$ Hz). The high frequency response was similar to that observed from the previous model, but the low frequency response showed some difference from the previous model. The frequency response of the TM 50 and 58 displacement to the TM 50 and 58 stiffness change (data not shown here) showed the exactly same characteristics as that of model-predicted stapes footplate displacement.

Change of Incudostapedial Joint Material Properties

Effect of material properties of the incudostapedial (I-S) joint on dynamic behaviors of middle ear system was examined using the FE model. FIGS. 8A and 8B shows the frequency response curves of the TM 50 and 58 (FIG. 8A) and stapes footplate (FIG. 8B) displacements predicted by the FE model when the Young's modulus of I-S joint was changed. The solid lines represent the normal Young's modulus of $6.0 \times 10^5$ Nm$^{-2}$ used for the I-S joint in the model. The thick and thin broken lines represent stiffer (10×normal Young's modulus) and softer (0.1×normal Young's modulus) I-S joints, respectively. As can be seen in FIGS. 8A and 8B, the material properties of I-S joint have substantial effect on the stapes footplate movement across the frequency range, but less effect on TM 50 and 58 movement. This suggests that change of mechanical properties of the I-S joint due to reconstruction of ossicular chain or implant on ossicles will have tremendous effect on stapes footplate movement and, thus affect hearing restoration level.

The stiffer I-S joint resulted in an overall increase of the stapes footplate displacement over the auditory frequency range (FIG. 8-B). This indicates that the sound energy was easily transferred to the stapes through the ossicular chain when the I-S joint became stiff. At the input port of the middle ear system (TM 50 and 58), the displacement was decreased (FIG. 8A), especially at low frequencies. However, the softer I-S joint resulted in an extensive reduction of stapes displacement (FIG. 8B) and an obvious increase of TM 50 and 58 displacement at low frequencies (FIG. 8A). One explanation for this phenomenon is that less sound energy was transported to the stapes through the softer joint connection so that the movement of the stapes was reduced significantly and the TM 50 and 58 movement was increased. These preliminary results predicted by the FE model about the effect of I-S joint on vibration transmission may provide useful information for design of middle ear implants or implantable hearing devices.

Change of Cochlear Load

Effect of cochlear fluid or cochlear load on acoustic-mechanical transmission from the TM 50 and 58 to stapes was predicted using the FE model of the ear. FIGS. 9A and 9B shows peak-to-peak displacements calculated from the model at the TM 50 and 58 (FIG. 9A) and stapes footplate (FIG. 9B) under intact and drained cochlea conditions. The intact cochlea had the impedance represented by the mass and viscous effects of cochlear fluid, which was assumed as a 25.5 mg mass connected with 10 dashpots. The drained cochlea was modeled without the cochlear mass and dashpots, and the stapes was supported by its annular ligament constraints only. When a simulation of an input sound pressure of 90 dB SPL was applied on the TM 50 and 58 in the external ear canal side, the displacements of the TM 50 and 58 and stapes footplate were calculated for the intact (solid lines) and drained cochlea (broken lines). Comparison of the FE model-derived results between the intact and drained cochleae showed that draining of cochlear fluid would increase stapes footplate displacements at high frequencies ($f \geq 1$ KHz, Panel B), the same results as obtained in measurements of 6 temporal bones using double laser Doppler interferometers.[8] However, the influence of cochlear load on TM 50 and 58 movement was very limited (FIG. 9A), similar to the inventor's observation from the temporal bones.

The displacements at the TM 50 and 58 and stapes footplate measured simultaneously by two laser interferometers in both control and drained cochlea cases of six bones showed that the TM 50 and 58 displacement essentially remained stable and unchanged during the control (i.e., intact) and drained cochlea experiments as reported by Gan et al.[8] Moreover, the displacement measured at the incus-stapes joint, a location away from the footplate, indicated less effect than that measured at the stapes due to the drainage of cochlear fluid in those six bones, which revealed that the major effect of cochlear impedance was on the stapes movement and there was very little effect on the TM 50 and 58 movement or the TM 50 and 58 input impedance. Thus, the present FE model has well predicted the effect of cochlear load on movements of the TM 50 and 58 and ossicles.

III. Acoustic—Structural Coupled Analysis

As the first step toward multi-field FE analysis of the entire ear, the acoustic-structural coupled analysis between the external ear canal air column and TM 50 and 58 or "one-chamber" acoustic-structural analysis was performed. A sound pressure of 90 dB was applied at the entrance of the ear canal. The acoustic pressure distribution along the canal and the mechanical movements at TM 50 and 58 and stapes footplate were calculated from the model. The results show that acoustic pressure was uniformly distributed in the canal at low frequencies ($f \leq 1$ KHz). At high frequencies ($f > 1$ KHz), the pressure distribution varied along the ear canal. FIGS. 10A and 10B shows acoustic pressure distributions at 4 KHz (FIG. 10A) and 8 KHz (FIG. 10B), respectively. These results indicate that acoustic pressure distribution in the ear reflects the superposition between the incident and reflected waves in the canal from the TM 50 and 58 and canal wall, which is closely related to the frequency. The results in FIG. 10 also demonstrated the beneficial role of the ear canal for enhancing sound intensity at higher frequencies.

FIGS. 11A and 11B shows the model-predicted frequency response curves of the displacements at tympanic membrane (FIG. 11A) and stapes footplate (FIG. 11B). The solid lines represent the results obtained from dynamic structural analysis when the sound pressure of 90 dB was applied on the lateral surface of the TM 50 and 58. The broken lines represent the displacements calculated from acoustic-structural coupled analysis when the same 90 dB SPL was input, respectively, at the canal entrance (thick broken lines) and at the 4 mm away from the TM 50 and 58 (umbo) in the ear canal (thin broken lines). The results clearly revealed that the external ear canal structure resulted in peak responses of both TM 50 and 58 and stapes footplate at frequencies between 3 and 4 KHz, which is consistent with a statement about external ear canal physical function for sound transmission addressed in anatomy textbooks.[2]

Discussion

The 3-D FE model of human ear in this study is preferably built on a complete set of histological sections of a human temporal bone, thus the model was characterized by accurate structural dimensions and geometric shapes of the middle ear, external ear canal, and middle ear cavity. The model was first validated for structural analysis of movements at the TM 50 and 58 (umbo) and stapes footplate by using a plurality, such as five, independent experimental measurements. The evaluation results show that the FE model predictions match the experimental results well and the model is able to predict structural dynamic behaviors of the middle ear. The validated FE model was then conducted for several otological applications to predict the effects of TM 50 and 58 thickness, TM 50 and 58 stiffness, I-S joint material properties, and cochlear load on acoustic-mechanical transmission through the middle ear. These results suggest that the FE model is potentially useful in the study of middle ear biomechanics and design and testing of middle ear implants and implantable hearing devices.

The external ear canal and middle ear cavity in the model are two important new components that were not constructed in the inventor's previous model. Especially, the middle ear cavity in this model is the first ever FE model with accurate geometry. By involving these two components, the model was much improved to simulate the dynamic behaviors of acoustic-structural coupled system of the ear. As the first step toward multi-field FE analysis of the entire ear, the pressure distribution in the ear canal and its effect on sound transmission were investigated. The acoustic-structural coupled FE analysis demonstrated that the peak values of displacements at the TM 50 and 58 (umbo) and stapes footplate occurred at frequencies of 3 to 4 KHz only when sound pressure was applied at the entrance of the canal (FIG. 11). It shows that the geometric configuration of ear canal determines physical function of the canal for sound transmission. In fact, the acoustic pressure distribution along the ear canal is related to frequency. The results from acoustic-structural coupled analysis of ear canal and ossicles have revealed that the sound pressure was not uniformly distributed across the canal at frequencies greater than 1 KHz. The absolute value of sound pressure was increased at the region near the TM 50 and 58 at frequencies around 3 and 4 KHz (FIG. 10). The enhanced sound pressure near the TM 50 and 58 resulted in maximum movements of the TM 50 and 58 and footplate at the corresponding frequencies. The mechanism for acoustic-mechanical transmission through the ear canal to the middle ear was demonstrated by this model.

Three openings on the middle ear cavity wall: the oval window and round window on the medial wall and the Eustachian tube opening on the anterior wall are shown in FIG. 4. The oval window niche is occupied by the stapes footplate and its annular ligament, providing a sealed but mobile communication between the middle ear and the vestibule, thus the area of the oval window should be slightly lager than the footplate. The published anatomical size of the round window membrane is about 2 mm vertically and 1.7 mm horizontally.[2] The Eustachian tube or the auditory tube serves to equalize the air pressure on both sides of the tympanic membrane, and to allow for drainage of the middle ear by serving as a portal into the nasopharynx. The diameter of Eustachian tube opening into the middle ear cavity is about 3.0 to 6.0 mm.[9] Compared with these published data, the calculated surface areas for the oval window (3.97 mm$^2$), round window (2.05 mm$^2$), and Eustachian tube opening (7.37 mm$^2$) in the model are within the reasonable range of values. This indicates that the FE model of the middle ear cavity created in this study is accurate and can be used for future multi-field FE analysis of the entire ear. The further utility of this model for pathological and reconstructed ears such as perforations of the tympanic membrane, otosclerosis, and Eustachian tube dysfunction will be certainly extended with the multi-field coupled FE analysis.

The model needs to be further improved in several aspects such as finding more accurate boundary conditions and adding the structure of cochlea and the cochlear fluid into the model. More FE models from different temporal bones are also needed for investigating the effect of individual temporal bones on functions of the ear. In conclusions, the model and the work reported here serve one step forward from the previous model toward the inventor's long-term goals: to develop a comprehensive 3-D FE model of human ear for multi-field FE analysis of ear biomechanics and otological applications.

Thus, an accurate, comprehensive finite element model of the human ear can provide better understanding of sound transmission, and can be used for assessing the influence of diseases on hearing and the treatment of hearing loss. The present invention relates to a 3-dimensional finite element model of the human ear which included the external ear canal, tympanic membrane (eardrum), ossicular bones, middle ear suspensory ligaments/muscles, and middle ear cavity. This model was constructed based on a complete set of histological section images of a left ear temporal bone. The finite element (FE) model of the human ear was validated by comparing model-predicted ossicular movements at the stapes footplate and tympanic membrane with published experimental measurements on human temporal bones. The FE model was employed to predict the effects of eardrum thickness and stiffness, incudostapedial joint material, and cochlear load on acoustic-mechanical transmission through the human ossicular chain. The acoustic-structural coupled FE analysis between the ear canal air column and middle ear ossicles was also conducted and the results revealed that the peak responses of both tympanic membrane and stapes footplate occurred between 3000 and 4000 Hz.

B. "Two-Chamber" Analysis and Model

The "two-chamber" acoustic-structural coupled analysis describes an acoustic-structural-acoustic coupling effect of the ear, such as the ear canal (one-chamber)—TM 50 and 58 and ossicles (structural)-middle ear cavity (second chamber).

Methods

I. 3D Finite Element Model

A 3D FE model of human left ear was created based on 780 histological sections of 20 μm thickness from a left ear temporal bone by the inventor and described in previous sections[36]. To facilitate the acoustic-structural-acoustic coupled analysis or "two-chamber" FE analysis, the mesh of the FE model was slightly modified. The TM 50 and 58 was meshed by 1,123 six-noded pentahedral elements instead of shell elements because the coupled analysis between the air in the ear canal, structures of the TM 50 and 58 and ossicles, and the air in the middle ear cavity requires the TM 50 and 58 as a three dimensional solid structure. Accordingly, the tympanic annulus was meshed by 130 six-noded pentahedral elements instead of shell elements although the shape and number of elements can be varied. The third modification was that the stapedial annular ligament was meshed using 50 three-noded shell elements instead of spring elements although the type and number of elements can be varied. Other meshes of the FE model remained the same as that reported by Gan et al.[36]. For instance, the ossicular bones were meshed by 6,663 four-noded tetrahedral elements. The incudomalleolar joint, incudostapedial joint, and manubrium that connects the malleus handle to the TM 50 and 58, were meshed by 655 four-noded elements (FIG. 2). The characteristic dimensions of the external ear canal, middle ear components, and middle ear cavity of the model have been reported in a recently published paper[36].

The human middle ear was described as a linear system under regular sound intensity of the hearing level for acoustic-mechanical transmission from the TM 50 and 58 to cochlea. The ossicles, ligaments, and tendons were assumed as isotropic materials while the TM 50 and 58 was assumed as orthotropic material. The mechanical properties of the TM 50 and 58, ossicles, joints, and manubrium in the model (Table 1A) were adopted based on previous investigation[36]. The Poisson's ratio was still assumed 0.3 for all materials of the system. The Raleigh damping parameters α and β for all materials of the system were assumed to be $0s^{-1}$ and $0.75 \times 10^{-4}s$, respectively.

It is worthy to note that the non-linear viscoelastic behavior of TM 50 and 58 has been shown by Gaihede and Koefoed-Nielsen[37] based on measurement of compliance or hysteresis of the middle ear system. Considering that the acoustic loading on the TM 50 and 58 was about 1 Pa (90 dB SPL) and the maximum displacement response was less than 1 μm in the current study, the assumption of linear material properties should be appropriate for the FE analysis. However, the non-linear material properties of the TM 50 and 58 should be investigated and incorporated if the high intensity sound appears.

The structural boundaries of the middle ear included tympanic annulus, middle ear suspensory ligaments or muscles, stapedial annular ligament, and cochlear fluid. The effect of cochlear fluid on acoustic-mechanical transmission through the ossicular chain was modeled as a mass block with 10 dashpots (5 on each side) attached between the stapes footplate and fixed bony wall, which represented distributed damping dominant impedance. The damping coefficient of each dashpot was calculated as 0.02 N-s/m. This assumption and calculation of cochlear load was based on the experimental studies of cochlear impedance on human temporal bones[1, 20] and the circuit model calculation for effective mass of the cochlear fluid[31, 17 and 20]. The Young's moduli for suspensory ligaments and muscles, and tympanic annulus (Table 2A) were assumed the same as the previous structural analysis[36]. The ear canal was open to the atmosphere, the same situation as the experimental setup in temporal bones in the inventor's laboratory. Thus, the boundary condition at the ear canal entrance was set free.

II. Acoustic-Structural Coupled FE Analysis

The ear consists of solid structures (ossicles and soft tissues), acoustic media (air in the ear canal and middle ear cavity), and fluid (cochlear fluid), which belong to different engineering disciplines and result in different boundary conditions, element attributes and model parameters as discussed above with reference to FIG. 2. Thus, the study of sound transmission through the ear requires multi-field coupled FE analysis. In this study, the canal-TM 50 and 58 and ossicles-middle ear cavity or "two-chamber" (ear canal and middle ear cavity) coupled analysis was conducted on the FE model. The air in the external ear canal and inside the middle ear cavity was modeled as acoustic elements and governed by the simplified acoustic wave equation under the assumptions that the fluid is compressible and inviscid with uniform mean density and pressure:

$$\frac{1}{c^2}\frac{\partial^2 P}{\partial t^2} - \nabla^2 P = 0 \quad (2)$$

where P is acoustic pressure, c is speed of sound and $c=\sqrt{k/\rho_o}$ in fluid medium, $\rho_o$ is mean fluid density, k is bulk modulus of fluid, and t is time. Equation (2) is the same as Equation (1) discussed above for consistency. The speed of sound and density of the air were assumed as 343 $ms^{-1}$ and 1.21 $kgm^{-3}$, respectively. At the acoustic-structure interfaces (e.g., the lateral and medial surfaces of the TM 50 and 58) where the pressure gradient of the air is related to the normal acceleration of the structure by fluid momentum equations, the discretized wave equation can be coupled with discretized structural equation[3]. Thus, coupling is handled by calculating element stiffness matrices and element load vectors that contain all necessary degrees of freedom.

In this "two-chamber" acoustic-structural-acoustic analysis, there were at least two types of interfaces between the air media and solid structure based on acoustic transmission feature on the interface. The surface of acoustic elements (air) next to the fixed structure such as the canal wall and middle ear cavity wall, was defined as "impedance surface", assigned with specified acoustic absorption coefficient μ (μ=1 for full sound absorption). The surface of acoustic elements next to the movable structure such as the TM 50 and 58, ossicles, and suspensory ligaments, was defined as fluid-structural interface (FSI) where the acoustic pressure distribution was coupled into structural analysis as the force input in ANSYS (ANSYS Inc., Canonsburg, Pa.). The TM 50 and 58 (both pars tensa 58 and pars flaccida 50) had two FSI's on its lateral and medial sides, respectively.

The acoustic absorption coefficient of FSI (μ) is defined as the fraction of absorbed acoustic energy to total incident energy[38,39] and can be calculated using the following equation for normal incidence:

$$\mu(\omega) = \frac{4\rho_I c_I \rho_{II} c_{II}}{(\rho_I c_I + \rho_{II} c_{II})^2} \qquad (3)$$

where ω is circular frequency, $\rho_I$ and $c_I$ represent density and sound speed of the incidental media, while $\rho_{II}$ and $c_{II}$ represent density and sound speed of the refracted media. Using Eq. (3), the acoustic absorption coefficients were calculated for four different interfaces between the air and structure in the FE model: 1) FSI's on the lateral and medial surfaces of the TM 50 and 58; 2) impedance surfaces between the air and canal wall or middle ear cavity wall; 3) FSI's between the air and ossicular bones; and 4) FSI's between the air and middle ear ligaments/muscle tendons. Exemplary absorption coefficient values are: 0.007 (TM 50 and 58), 0.02 (canal wall) and 0.04 (cavity wall), 0.04 (ossicles), and 0.02 (ligaments), respectively, although these may be varied.

III. Acoustic Pressure Measurement on Human Temporal Bones

Five fresh-frozen, cadaveric temporal bones (2 male and 3 female), obtained through the University of Oklahoma Health Sciences Center, were used in this study. The donors' average age was 77.2. The preparation of temporal bone specimen with intact cochlea was the same as reported in the inventor's previous papers about the middle ear transfer function measurement on human temporal bones[6,7,8]. Briefly, pure tone, narrow band, filtered sound signals from a function generator (such as a Model 193, Wavetek, San Diego, Calif.) were delivered to the TM 50 and 58 by an insert earphone (such as a Model ER-2, Etymotic Research, Elk Grove Village, Ill.) and monitored by two probe microphones (such as a Model ER-7, Etymotic Research). The first probe tube was placed in the canal approximately 2 mm away from the umbo. The second probe was placed between the round window and stapes (near the IS joint) and cemented to the bone after facial recess surgical approach. The middle ear cavity was then closed such as by filling dental cement (Reprosil, DDI Inc., Milford, Del.) although other fillers may be used. Both pressure probes were connected to a digitizing signal analyzer (such as a Model DSA 601, Tektronix, Beaverton, Oreg.) and the spectral magnitude and phase information of acoustic pressure were recorded simultaneously.

Results

I. Acoustic Pressure Distributions in Ear Canal and Middle Ear Cavity (Normal Ear)

The FE model of normal ear was first validated by comparing the frequency response curve of acoustic pressure near the umbo in the ear canal with the published experimental data. The harmonic 90 dB sound pressure level (0.632 N/m², rms value) was applied at the entrance of the canal and the acoustic-structural coupled FE analysis was conducted over the frequency range of 0.2-10 kHz using, e.g., ANSYS on a PC (Dell Dimensions 4100). The magnitude of acoustic pressure at the TM 50 and 58 in the ear canal was calculated as shown in FIG. 12. The broken line is the FE model-derived pressure curve and the solid line is the experimental curve obtained by Shaw[40]. The FE result showed a 12 dB SPL increase of sound pressure around frequency 3.5 kHz with a pressure response pattern similar to the experimental result. The difference in peak frequency between the FE model (3.5 kHz) and experimental (2.5 kHz) results may be caused by different canal lengths in experimental subjects and the FE model.

The FE acoustic pressure distributions in the ear canal and middle ear cavity were obtained at frequencies of 1, 4, and 8 kHz when sound pressure of 90 dB SPL was input at the locations of 2 mm and 10 mm away from the umbo, and the canal entrance, respectively (FIG. 13). The results demonstrated that acoustic pressure distributions in both ear canal and middle ear cavity are functions of frequency and sound source location. At low frequencies (f≦1 kHz), the acoustic pressure was uniformly distributed in the canal and middle ear cavity and the pressure level was not affected by the location of input sound source (left column panels in FIG. 13). At high frequencies (f>1 kHz), the pressure distribution varied along the canal and the pressure value (magnitude) was sensitive to the location of input sound. For instance, the sound pressure near the TM 50 and 58 varied from 0.89 to 1.10 to 3.29 N/m² (equivalent to 93, 94.8, and 104 dB SPL, respectively) at frequency of 4 kHz when 90 dB input sound pressure was applied at the locations of 2 mm and 10 mm away from the umbo, and the canal entrance, respectively (middle column panels in FIG. 13). At frequency of 8 kHz, the pressure changed from 0.92 to 4.37 to 1.88 N/m² (or 93.3, 106.8, and 99.5 dB SPL) as the input sound location varied from 2 mm, to 10 mm away from the umbo, and to the canal entrance (28 mm away from the umbo) (right column panels in FIG. 13). These results reflect superposition of the incident and reflected sound waves from the TM 50 and 58 and canal wall in the canal. The superposition is closely related to the frequency and location of input sound source. Moreover, there were no significant changes of acoustic pressure near the umbo with frequency while the input sound was applied at 2 mm from the umbo (bottom row in FIG. 13).

FIGS. 14A and 14B show the FE model-predicted frequency response curves of acoustic pressure at several different locations in the canal and middle ear cavity when a harmonic sound pressure of 90 dB SPL was applied at the canal entrance with open ear canal. FIGS. 14A and 14B display the magnitude and phase angle of the acoustic pressure, respectively. The thick lines represent the results at different positions in the ear canal such as the umbo, 2 mm and 10 mm away from the umbo. The thin lines represent the pressures at four specific locations in the middle ear cavity such as the oval window, IS joint, round window, and umbo. The results showed that the pressure responses at four locations in the cavity were almost identical at frequencies below 3.5 kHz. At high frequencies (f>3.5 kHz), the difference of magnitude was within 5 dB, while the phase difference was within 20 degrees. It was also noticed that the phase of the pressure in the middle ear cavity is more advanced than that in the ear canal at low frequencies. The similar phase lag at low frequencies was observed when the input sound was delivered at 2 mm away from the umbo in the ear canal side. The reason of this phenomenon remains to be further studied. The variations of pressure responses with locations in the ear canal were observed at frequencies higher than 1 kHz and the pressure at 10 mm away from the umbo displays a deep drop around 8 kHz, an obvious difference from other two locations tested. This result is consistent with the pressure distribution shown in the middle row of FIG. 13 where a broad low-pressure region in the middle of the canal was observed at 8 kHz.

II. Acoustic Pressure Distributions in Ear Canal and Middle Ear Cavity (Pathological Ear)

The FE model of the ear was used for predicting changes of sound pressure distribution in the ear canal and middle ear cavity under middle ear structural alterations or pathological conditions such as TM 50 and 58 perforations. Two types of TM 50 and 58 perforations were created in the FE model to simulate the cadaveric TM 50 and 58 in human temporal bone experimental studies (FIG. 15). A perforation 100 (Case #1) was made in an inferior-posterior site 102 of the TM 50 and 58 with a perforation area of 1.32 mm$^2$ (1.84% of TM 50 and 58 surface area). A second perforation 104 (Case #2) was made in an inferior site 106 with an area of 0.82 mm$^2$ (1.14% of TM 50 and 58 surface area). Also shown in FIG. 15 is a pars flacida 50, a pars tensar 58, and a tympanic annulus 52.

The spatial acoustic pressure distributions in the ear canal and middle ear cavity for the TM 50 and 58 perforations 100 and 104 (i.e., Case #1, Case #2, and combination of Cases #1 and #2) showed that the pressure in the ear canal was uniformly distributed along the canal at low frequencies (f≦1 kHz). For instance, the acoustic pressure near the umbo was about 0.90-1.04 N/m$^2$, the same values as that shown in FIG. 13 of the normal ear, when the input sound of 90 dB SPL (0.632 N/m$^2$) was applied at the canal entrance, 10 mm or 2 mm away from the umbo. This indicated that the TM 50 and 58 perforation would not affect pressure distributions in the canal at low frequencies. However, the pressure in the ear canal was reduced at high frequencies (f≧4 kHz) for perforated ears, especially, for the combined two-perforation case. The pressure near the umbo for intact TM 50 and 58 (top row of FIG. 13) was 3.29 and 1.88 N/m$^2$ at frequencies of 4 and 8 kHz, respectively. For perforated TM 50 and 58, the corresponding pressure values at 4 and 8 kHz changed to 1.15 and 1.50 N/m$^2$ (Case #1), 1.49 and 1.46 N/m$^2$ (Case #2), and 0.67 and 1.21 N/m$^2$ (combination of Cases #1 and #2), respectively.

Acoustic pressure in the middle ear cavity increased significantly at the frequency range of 0.2-10 kHz when the TM 50 and 58 perforation occurred. FIGS. 16-18 displayed acoustic pressure variations with frequencies at four locations inside the middle ear cavity: near the oval window, IS joint, round window, and umbo, for the inferior-posterior perforation 100 (Case #1), inferior perforation 104 (Case #2), and combination of Cases #1 and #2, respectively. The thin solid and broken lines represented the pressures at those locations. The input sound was applied at 2 mm away from the umbo in the ear canal (thick-broken lines in FIGS. 16-18). Compared to the ear with intact or normal TM 50 and 58 (FIG. 14), the pressure response (magnitude) in the middle ear cavity increased to 90 dB at low frequencies (f<1 kHz) for perforation 100 Case #1 (FIGS. 16A and 16B) and 104 Case #2 (FIGS. 17A and 17B). The cavity pressure reached peak value of 94 dB at 3 kHz for both perforations 100 and 104. With frequency increasing, the phase angle decreased from zero at low frequencies and there were no zero cross-over observed in phase curves for TM 50 and 58 perforation cases (FIGS. 16-18). This indicated different characteristics between perforated and normal ears. Moreover, the cavity pressure curves showed much less phase delay in the TM 50 and 58 perforated ears than the normal ears.

Finally, the FE model-predicted frequency response curves of acoustic pressure in the middle ear cavity (near the IS joint) were compared with the experimental data obtained in human temporal bones (FIGS. 19A-D). During temporal bone experiments, sound pressure measurements were made first with the TM 50 and 58 normal and then with the perforation Case #1 and Case #2 created using a special surgical tool. Upon the completion of measurement in perforation 100 (Case #1), the perforation in the inferior site of the TM 50 and 58 104 (Case #2) was made and the hole in the inferior-posterior site of the TM 50 and 58 (Case #1) was patched, such as with cigarette paper[41]. Finally, the patch, e.g., cigarette paper was removed and measurement was made with combination of Cases #1 and #2.

FIG. 19A displays pressure curves measured from five normal temporal bones with the normal TM 50 and 58 (control study). FIGS. 19B, 19C, and 19D display pressure curves measured from temporal bones with the inferior-posterior, inferior, and combined inferior-posterior and inferior TM 50 and 58 perforations. Some variations (FIG. 19A) existed among five bones in control group, but the FE curve was consistent with the general pattern of the experimental pressure response in the middle ear cavity. The FE frequency response curves for TM 50 and 58 perforation cases were fit very well with the temporal bone experimental data (FIGS. 19B, 19C, and 19D).

Discussion

The characteristics of sound pressure transmission from the external ear canal to the middle ear has been revealed through acoustic-structural-acoustic "two-chamber" coupled analysis using the FE model of human ear. The acoustic pressure distributions in the normal ear canal and middle ear cavity are spatially visualized and quantified in the canal and middle ear cavity of the FE model (FIG. 13). In addition to the spatial visualization of pressure distributions, the frequency response curves of acoustic pressure magnitude and phase angle can be also obtained at any point in the ear canal and middle ear cavity using this model. As an example, the acoustic pressure responses across auditory frequency range of 0.2 to 10 kHz at several locations in the canal and middle ear cavity were shown in FIGS. 14A and 14B. Note that the absolute value of sound pressure in the middle ear cavity is expected to vary with the air volume of the cavity. In the present study, the FE model was created from one temporal bone and the middle ear cavity did not include the mastoid air cells. Thus, the effect of the variation of middle ear cavity volume on pressure distribution inside the cavity was not involved in this study. However, the FE model has been extended to pathological studies on acoustic functions in the external ear canal and middle ear cavity. It is worthy to note that the utilization of the FE model for acoustic-structural coupled analysis is not limited to what was presented here. Therefore, the FE model provides a useful analysis tool for study of acoustic transmission in human ear.

In this description, the acoustic functions of normal ear canal were first examined by using the FE model to investigate the ear canal sound pressure gain. The sound pressure gain predicted by the FE model was 12 dB SPL (FIGS. 12 and 14) that was exactly the same amount as the experimental data measured by Shaw[40]. The model-predicted pressure gain was reached at 3.5 kHz, the resonant frequency of the isolated ear canal without attached pinna. This result demonstrated an important acoustic function of the ear canal for enhancing the sound pressure level on lateral surface of the TM 50 and 58[42].

It is important to accurately measure sound pressure at the TM 50 and 58 for clinical examination and in vitro cadaveric human temporal studies. During the inventor's temporal bone experiments, the probe microphone was usually placed at about 2 mm away from the umbo in the ear canal[6-8]. The sound pressure level at the TM 50 and 58 was assumed uniformly distributed and independent of frequency when sound was monitored at 2 mm from the umbo. Using the coupled acoustic-structural analysis on the FE model, the effect of probe microphone location in the canal on the sound pressure measurement was examined and this assumption was verified for the normal ear (FIG. 13) and the TM 50 and 58 perforated ears (figures not shown). Using the FE model, it was also predicted that the actual sound pressure level at 4 kHz near the TM 50 and 58 would be underestimated by 6 dB SPL if the probe microphone were placed at the entrance of the ear canal instead of 2 mm from the umbo. This result is consistent to the observations reported by Dirks and Kincaid[43] about ear canal probe measurements.

Compared with acoustic functions of the ear canal, sound pressure in the middle ear cavity displayed different frequency response characteristics. The acoustic pressure in the middle ear cavity were 10-20 dB lower than that near the umbo in the canal over the frequency range of 0.2-10 kHz (FIG. 14A). Such a big drop of acoustic pressure in the cavity, compared with the canal pressure, was caused by high acoustic impedance of the TM 50 and 58 that was induced by attached middle ear and inner ear structures. In the FE coupled analysis, the structural effect was taken into the consideration for acoustic impedance. Thus, the air vibration in the middle ear cavity was almost 3 orders of magnitude lower than the air vibration in the canal. On the presence of perforations in the TM 50 and 58, the TM 50 and 58 impedance was reduced and the sound wave was allowed to enter the middle ear cavity. Thus, the resonant pressure peaks were flattened in the canal and the acoustic pressure in the middle ear cavity was increased.

Effects of the TM 50 and 58 perforation size and location on sound transmission and pressure distributions in the ear canal and middle ear cavity were investigated through three steps in this study. First, the acoustic pressure distributions in the ear canal and middle ear cavity were quantitatively visualized for ears with different perforation sizes and locations in the TM 50 and 58 (figures not shown). Next, the frequency responses of sound pressures at different locations in the middle ear cavity were investigated for the ears with different perforation sizes and locations (FIGS. 16-18). Finally, the FE model-predicted spectral curves of acoustic pressure in the cavity were compared with the experimental data measured in five human temporal bones (FIG. 19A-D). Based on the FE results, the following conclusions can be drawn:

1) The TM 50 and 58 perforation reduced sound pressure difference across the TM 50 and 58, especially at low frequencies (f<1 kHz). This observation is consistent with experimental measurements obtained in the inventor's temporal bone studies as well as reported by Voss et al.[41, 44].

2) There was no significant effect of the TM 50 and 58 perforation location on acoustic pressure distribution and frequency response in the middle ear cavity for small perforation size. The perforation area ratio tested in this study was less than 2% of the TM 50 and 58 surface area. For large perforation ratio, for example, 20-30%, the perforation location may affect the pressure distribution and frequency response.

3) The perforation size had profound influence on acoustic pressure distribution and frequency characteristics in the middle ear cavity. The larger perforation in the TM 50 and 58 (combination of Cases #1 and #2 in FIG. 15) resulted in a higher peak pressure value and a higher resonant frequency than the small or single perforation (FIGS. 16-18).

4) There was no significant difference of the acoustic pressure measured at different locations in the middle ear cavity, especially at low frequencies (f<3 or 4 kHz). As frequency increased (f>4 kHz), the pressure difference between the stapes (or oval window) and round window was detected and increased with a maximum of 5 dB at 10 kHz. This demonstrated that the window pressure difference (the oval and round windows) or the "acoustic pathway" for sound transmission to the inner ear is insignificant. The same conclusion was obtained from experimental measurements on temporal bones by Voss et al.[44] and Peake et al.[45].

The inventor believes that both pressure distribution and transfer function studies will provide a complete description on the coupled acoustic-structural analysis for the sound transmission from the external ear canal to the middle ear. The model will be further improved to simulate middle ear alterations caused by middle ear diseases such as the otitis media with effusion. As one long-term goal, several standard FE models will be developed for different population groups that are based on different specific criterions such as anatomy, age, gender, and race. It is expected that the future study will be able to determine how the alterations in structure and mechanical properties of human ear affect the acoustic-mechanical transmission through the external ear canal and middle ear to inner ear in normal, pathological and reconstructed ears.

REFERENCES

The following references are hereby incorporated by reference to the extent that such references teach exemplary procedures utilized in accordance with the present invention.

[1] Aibara, R., J. T. Welsh, S. Puria, and R. L. Goode. Human middle-ear sound transfer function and cochlear impedance. *Hear. Res.* 152:100-109, 2001.

[2] Canalis, R. F. and P. R. Lambert. The EAR—Comprehensive Otology. Philadelphia: Lippincott Williams & Wilkins, 2000.

[3] Cho, J. R., H. W. Lee, and K. W. Kim. Free vibration analysis of baffled liquid-storage tanks by the structural-acoustic finite element formulation. *J. Sound and Vibration*, 258(5): 847-866, 2002.

[4] Donaldson, J. A. and J. M. Miller. "Anatomy of the Ear". In: *Basic Sciences and Related Disciplines, Otolaryngology*, Vol. 1. Philadelphia: Saunders, 1973, pp. 75-110.

[5] Funnell, W. R. J. and C. A. Laszlo. Modeling of the cat eardrum as a thin shell using the finite-element method. *J Acoust Soc Am.* 63:1461-1467, 1978.

[6] Gan, R. Z., R. K. Dyer, M. W. Wood, and K. J. Dormer. Mass loading on ossicles and middle ear function. *Ann Otol Rhinol Laryngol.* 110 (5):478-485, 2001.

[7] Gan, R. Z., Q. Sun, R. K. Dyer, K-H Chang, and K. J. Dormer. Three dimensional modeling of middle ear biomechanics and its application. *Otology & Neurotology,* 23(3):271-280, 2002.

[8] Gan, R. Z., M. W. Wood, and K. J. Dormer. Human middle ear transfer function measured by double laser interferometry system, *Otology & Neurotology,* Vol. 25, No. 4, 423-435, 2004.

[9] Gelfand, S. A. Hearing—An Introduction to Psychological and Physiological Acoustics. New York: Murcel Dekker, 1998, pp. 43-44.

[10] Goode, R. L., M. Killion, K. Nakamura, and S. Nishihara. New knowledge about the function of the human middle ear: development of an improved analog model. *Am J Otol.* 15: 145-154, 1994.

[11] Herrmann, G. and H. Liebowitz. "Mechanics of bone fractures". In: *Fracture: An Advanced Treatise,* edited by H. Liebowitz. New York: Academic Press, 1972, pp. 772-840.

[12] Hudde, H. and C. Weistenhöfer. A three-dimensional circuit model of the middle ear. *Acustica United with Acta Acustica,* 83 (3):535-549, 1997.

[13] Kelly, D. J., P. J. Prendergast, and A. W. Blayney. The effect of prosthesis design on vibration of the reconstructed analysis of four prostheses. *Otology & Neurotology.* 24:11-19, 2003.

[14] Kirikae, I. *The Structure and Function of the Middle Ear.* Tokyo: University of Tokyo Press, 1960.

[15] Koike, T. and H. Wada. Modeling of the human middle ear using the finite-element method. *J Acoust Soc Am.* 111(3):1306-1317, 2002.

[16] Kringlebotn, M. and T. Gundersen. Frequency characteristics of the middle ear. *J Acoust Soc Am.* 77:159-164, 1985.

[17] Kringlebotn, M. Network model for the human middle ear. *Scan Audiol.* 17: 75-85, 1988.

[18] Lutman, M. E. and A. M. Martin. Development of an electroacoustic analogue model of the middle ear and acoustic reflex. *J Sound & Vibration.* 64(1):133-157, 1979.

[19] Lynch, T. J., V. Nedzelnitsky, and W. T. Peake. Input impedance of the cochlea in cat. *J Acoust Soc Am.* 72:108-130, 1982.

[20] Merchant, S. N., M. E. Ravicz, and J. J. Rosowski. Acoustic input impedance of the stapes and cochlea in human temporal bones. *Hear. Res.* 97:30-45, 1996.

[21] Nishihara, S. and R. L. Goode. "Measurement of tympanic membrane vibration in 99 human ears". In: *Research and Otosurgery: Proceedings of the International Workshop on Middle Ear Mechanics in Research and Otosurgery,* edited by K. B. Hüttenbrink KB: Dresden, Germany, Dresden University Press, 1997, pp. 91-93.

[22] Prendergast, P. J., P. Ferris, H. J. Rice, and A. W. Blayncy. Vibro-acoustic modeling of the outer and middle ear using the finite element method. *Audiol Neurootol.* 4(3-4): 185-191, 1999.

[23] Rabbitt, R. D. and M. H. Holmes. A fibrous dynamic continuum model of the tympanic membrane. *J Acoust Soc Am.* 80(6):1716-1728, 1986.

[24] Rosowski, J. J. and S. N. Merchant. Mechanical and acoustic analysis of middle ear reconstruction. *Am J Otol.* 16:486-497, 1995.

[25] Sun, Q., K-H. Chang, K. J. Dormer, R. K. Dyer, and R. Z. Gan. An advanced computer-aided geometric modeling and fabrication method for human middle ear. *Medical Engineering and Physics.* 24:596-606, 2002.

[26] Sun, Q., R. Z. Gan, H-K. Chang, and K. J. Dormer. Computer-integrated finite element modeling of human middle ear. *Biomechanics and Modeling in Mechanobiology,* 1:109-122, 2002.

[27] Von Békésy G. *Experiments in hearing.* New York: McGraw-Hill, 1960.

[28] Wada, H. and T. Metoki. Analysis of dynamic behavior of human middle ear using a finite method. *J Acoust Soc Am.* 92(6):3157-3168, 1992.

[29] Wada, H., T. Koike, and T. Kobayashi. "Three-dimensional finite-element method (FEM) analysis of the human middle ear". In: *Research and Otosurgery: Proceedings of the International Workshop on Middle Ear Mechanics in Research and Otosurgery,* edited by K. B. Hüttenbrink K B: Dresden, Germany, Dresden University Press, 1997, pp. 76-80.

[30] Wever, E. G. and M. Lawrence. Physiological Acoustics. Princeton: Princeton University Press, 1982.

[31] Zwislocki, J. Analysis of the middle ear function. Part I. Input impedance. *J Acoust Soc Am.* 34: 1514-1523, 1962.

[32] Mller A R. Network model of the middle ear. *J Acoustic Soc Am;* 33:168-176, 1961.

[33] Shaw E A G, Stinson M R. Network concepts and energy flow in the human middle ear. *J Acoust Soc Am;* 69:S43, 1981.

[34] Feng B, Gan R Z. Lumped parametric model of human ear for sound transmission *Biomechanics and Modeling in Mechanobiology;* 3:33-47, 2004.

[35] Sun Q, Gan R Z, Chang H K, Dormer K J. Computer-integrated finite element modeling of human middle ear. *Biomechanics and Modeling in Mechanobiology;* 1: 109-122, 2002.

[36] Gan R Z, Feng B Sun Q. Three-dimensional finite element modeling of human ear for sound transmission *Annals of Biomedical Engineering;* 32(6):847-859, 2004.

[37] Gaihede M, Koefoed-Nielsen B. Mechanics of the middle ear system: Age-related changes in viscoelastic properties. *Audiol Neuro-otol;* 5(2):53-58, 2000.

[38] Pierce A D. Acoustics—An Introduction to its Physical Principles and Applications. McGraw-Hill, New York, 1981.

[39] Kinsler L E, Frey A R, Coppens A B, Sanders J V. Fundamentals of Acoustics. 4th edition, John Wiley & Sons, New York, 2000.

[40] Shaw EAG. The external ear. In: Keidel, W. D., Nef, W. D. (Eds.), Handbook of Sensory Physiology. Vol. 1, Berlin, Germany, Springer-Verlag, 1974.

[41] Voss S E, Rosowski J J, Merchant S N, Peake W T. 2001a. Middle-ear function with tympanic-membrane perforations. I. Measurements and mechanisms. *J Acoust Soc Am;* 110:1432-1444, 2001.

[42] Goode R L. Auditory physiology of the external ear. In: Jahn, A. F., Santos-Sacchi, J. (Eds.), *Physiology of the Ear.* $2^{nd}$ edition, Canada, Singular; p. 147-159, 2001.

[43] Dirks D D, Kincaid G E. Basic acoustic considerations of ear canal probe measurements. *Ear Hear;* 8:60S-67S, 1987.

[44] Voss S E, Rosowski J J, Merchant S N, Peake W T. How do tympanic-membrane perforations affect human middle-ear sound transmission? *Acta Otolaryngol;* 121:169-173, 2001.

[45] Peake W T, Rosowski J J, Lynch T J. Middle-ear transmission: Acoustic versus ossicular coupling in cat and human. *Hearing Res;* 57:245-268, 1992.

[46] Gan et al. Acoustic-structural coupled finite element analysis for sound transmission in human ear—Pressure distributions. *Medical Engineering & Physics.* 28:395-404, 2006.

Although the foregoing invention has been described in some detail by way of illustration and example for purposes of clarity of understanding, it will be apparent to those skilled in the art that certain changes and modifications may be practiced without departing from the spirit and scope thereof, as described herein and in the above-referenced attachments. Also, it is to be understood that the phraseology and terminology employed herein is for purpose of description and should not be regarded as limiting. The term "comprising" within the claims is intended to mean "including at least" such that the recited listing of elements in a claim are an open group. "A," "an" and other singular terms are intended to include the plural forms thereof unless specifically excluded.

What is claimed is:

1. A method for developing a computational model of an ear comprised of a plurality of individual anatomical structures, at least one of the anatomical structures including an external ear canal and a middle ear cavity filled with air, the method comprising the steps of:
   constructing, by a computer system, a three-dimensional geometric model of the ear including a plurality of anatomical structures of the ear, each anatomical structure having a physical property of at least one of air and solid material;
   meshing the individual anatomical structures in the three-dimensional geometric model of the ear accounting for the physical properties of the meshed anatomical structures;
   assigning material properties for the anatomical structures within the three-dimensional model based on the physical property of each anatomical structure;
   assigning boundary conditions to the three-dimensional model for at least some of the anatomical structures indicative of the interaction between such anatomical structures, the boundary conditions including at least one of an air-to-solid interface; and
   employing acoustic-structural coupled analysis calculating at least an acoustic pressure distribution along the external ear canal using the boundary conditions including the at least one air-to-solid interface on the three-dimensional model to generate data indicative of the acoustic effect on mechanical vibration transmission in the ear caused by introducing an acoustic wave into the air within the external ear canal.

2. The method of claim 1, wherein the three dimensional geometric model is constructed based on histological section images of a temporal bone of a human cadaver.

3. The method of claim 2, wherein the temporal bone includes the ear canal, eardrum, middle ear cavity, malleus, incus, stapes, cochlea and eustachian tube.

4. The method of claim 2, wherein the temporal bone is dissected into between 500 and 1000 histological sections.

5. The method of claim 1, further comprising the steps of:
   applying a simulation of harmonic sound pressure on a tympanic membrane from an ear canal side; and
   calculating the movement responses at different locations of a middle ear system and sound pressure in the middle ear cavity.

6. The method of claim 1, wherein the three dimensional geometric model includes the eardrum, the middle ear ossicular bones, and the middle ear suspensory ligaments or muscles.

7. The method of claim 1, wherein the three dimensional geometric model includes the external ear canal, the eardrum, the ossicular bones, the suspensory ligaments and the middle ear cavity.

8. The method of claim 1, wherein the three dimensional geometric model includes the external ear canal, the eardrum, the ossicular bones, the suspensory ligaments, the middle ear cavity, and the cochlea.

9. The method of claim 1, wherein the step of employing acoustic-structural coupled analysis to the anatomical structures of the ear is defined further as employing acoustic-structural-acoustic coupled analysis to model an ear canal, a tympanic membrane, and a middle ear cavity.

10. The method of claim 1, wherein the step of employing acoustic-structural coupled analysis is defined further as calculating element stiffness matrices and element load vectors.

11. A finite element model of an ear comprised of a plurality of individual anatomical structures of the ear, wherein at least one of the anatomical structures includes an external ear canal and a middle ear cavity filled with air, stored on one or more non-transitory computer readable medium and including logic that when executed by a computer causes the computer to:
   construct a three-dimensional geometric model of the ear including a plurality of anatomical structures of the ear, each anatomical structure having a physical property of at least one of air and solid material;
   mesh the individual anatomical structures in the three-dimensional model of the ear accounting for the physical properties of the meshed anatomical structures;
   assign material properties for each anatomical structure within the three-dimensional model based on the physical property of each anatomical structure;
   assign boundary conditions to the three-dimensional model for at least some of the anatomical structures indicative of the interaction between such anatomical structures, the boundary conditions including at least one of an air-to-solid interface; and
   employ acoustic-structural coupled analysis calculating at least an acoustic pressure distribution along the external ear canal using the boundary conditions including the at least one air-to-solid interface on the three-dimensional model to generate data indicative of the acoustic effect on mechanical vibration transmission in the ear caused by introducing an acoustic wave into the air within the external ear canal.

12. The finite element model of claim 11, wherein the three-dimensional geometric model is constructed based on histological section images of a temporal bone of a human cadaver.

13. The finite element model of claim 12, wherein the temporal bone includes the ear canal, eardrum, middle ear cavity, malleus, incus, stapes, cochlea and eustachian tube.

14. The finite element model of claim 12, wherein the temporal bone is dissected into between about 500 and 1000 histological sections.

15. The finite element model of claim 11, further comprising logic for applying a simulation of harmonic sound pressure on a tympanic membrane of the geometric model from an ear canal side and calculating the movement responses at different locations of a middle ear system and sound pressure in the middle ear system.

16. The finite element model of claim 11, wherein the three-dimensional geometric model includes the eardrum, the middle ear ossicular bones, and the middle ear suspensory ligaments or muscles.

17. The finite element model of claim 11, wherein the three-dimensional geometric model includes the external ear canal, the eardrum, the ossicular bones, the suspensory ligaments and the middle ear cavity.

18. The finite element model of claim 11, wherein the three-dimensional geometric model includes, the external ear canal, the eardrum, the ossicular bones, the suspensory ligaments, the middle ear cavity, and the cochlea.

* * * * *

UNITED STATES PATENT AND TRADEMARK OFFICE
CERTIFICATE OF CORRECTION

PATENT NO.      : 7,893,934 B2                                             Page 1 of 1
APPLICATION NO. : 11/441541
DATED           : February 22, 2011
INVENTOR(S)     : Rong Z. Gan It is certified that error appears in the above-identified patent and that said Letters Patent is hereby corrected as shown below:

Column 2, line 16: After "mechanics." delete "$^{15, 13, 17}$" and replace with -- $^{15, 13, 7}$ --

Signed and Sealed this
Fifteenth Day of November, 2011

David J. Kappos
*Director of the United States Patent and Trademark Office*